(12) United States Patent
Donner et al.

(10) Patent No.: US 8,124,338 B2
(45) Date of Patent: Feb. 28, 2012

(54) USE OF TDE FOR ISOLATION OF NUCLEIC ACIDS

(75) Inventors: Horst Donner, Penzberg (DE); Frank Bergmann, Iffeldorf (DE); Nina Lassonczyk, Penzberg (DE); Manfred Watzele, Weilheim (DE); Marcus Schmid, Wessobrunn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 136 days.

(21) Appl. No.: 12/481,807

(22) Filed: Jun. 10, 2009

(65) Prior Publication Data

US 2010/0086924 A1 Apr. 8, 2010

Related U.S. Application Data

(63) Continuation of application No. PCT/EP2007/010793, filed on Dec. 11, 2007.

(30) Foreign Application Priority Data

Dec. 13, 2006 (EP) .................................... 06025779

(51) Int. Cl.
*C12Q 1/68* (2006.01)
*C07H 21/02* (2006.01)
*C07H 21/04* (2006.01)

(52) U.S. Cl. ....... 435/6.1; 536/23.1; 536/24.3; 536/25.4

(58) Field of Classification Search ..... 435/6; 536/23.1, 536/24.3, 25.4

See application file for complete search history.

(56) References Cited

U.S. PATENT DOCUMENTS

| | | | |
|---|---|---|---|
| 5,004,543 A * | 4/1991 | Pluskal et al. ................ | 210/490 |
| 5,234,809 A | 8/1993 | Boom et al. | |
| 6,383,393 B1 | 5/2002 | Colpan et al. | |
| 6,905,825 B2 | 6/2005 | Kojima et al. | |
| 2001/0009960 A1* | 7/2001 | Sato et al. ........................ | 536/63 |
| 2002/0086326 A1* | 7/2002 | Smith et al. ........................ | 435/6 |
| 2002/0128364 A1* | 9/2002 | Michot et al. ................ | 524/401 |
| 2002/0164572 A1* | 11/2002 | Lin et al. ............................ | 435/2 |
| 2004/0019196 A1* | 1/2004 | Bair et al. ..................... | 536/25.4 |
| 2005/0059024 A1 | 3/2005 | Conrad | |
| 2005/0079535 A1 | 4/2005 | Kirchgesser et al. | |
| 2005/0123965 A1* | 6/2005 | Yamashita et al. ................ | 435/6 |
| 2006/0166368 A1 | 7/2006 | Berkelman | |

FOREIGN PATENT DOCUMENTS

| | | |
|---|---|---|
| DE | 3724442 A1 | 2/1989 |
| EP | 0768773 A1 | 10/1996 |
| WO | 9916781 A2 | 4/1999 |
| WO | 0137291 A1 | 5/2001 |
| WO | 2005012487 A2 | 2/2005 |

OTHER PUBLICATIONS

Bartl, K. et al., "Simple and Broadly Applicable Sample Preparation by Use of Magnetic Glass Particles," Clin Chem Lab Med 36:8 (1998) 557-559.
Boom, R. et al., "Rapid and Simple Method for Purification of Nucleic Acids," Journal of Clinical Microbiology 28:3 (Mar. 1990) 495-503.
Cox, A., "The Use of Guanidinium Chloride in the Isolation of Nucleic Acids," Methods Enzymol 12B (1968) 120-129.
Goessl, A. et al., "Plasma lithography-thin-film patterning of polymers by RF plasma polymerization II: Study of differential binding using adsorption probes," J.Biomater. Sci. Polymer Edn. 12:7 (2001) 739-753.
Jakobi, R. et al., "Filter-Supporter Preparation of λ Phage DNA," Analytical Biochemistry 175 (1988) 196-201.
Mullis, K. et al., "Specific Synthesis of DNA in Vitro via a Polymerase-Catalyzed Chain Reaction," Methods in Enzymology 15 (1987) 335-350.
Sambrook et al., Molecular Cloning, A Laboratory Manual, 3rd Edition, CSHL Press 2001.
Schmitt, M. et al., "A rapid and simple method for the preparation of RNA from *Saccaromyces cerevisiae*," Nucleic Acids Research 18:10 (1990) 3091-3092.
Stallcup, M. et al., "Region-specific Initiation of Mouse Mammary Tumor Virus RNA Synthesis by Endogenous RNA Polymerase II in Preparation of Cell Nuclei," The Journal of Biological Chemistry, 258:10 (1983) 2802-2807.
Vogelstein, B. et al., "Preparative and analytical purification of DNA from agarose," Proc. Natl. Acad. Sci. USA 76:2 (Feb. 1979) 615-619.
Watson, J. et al., "Molecular Structure of Nucleic Acids," Nature 171:4356 (1953) 737-738.

\* cited by examiner

*Primary Examiner* — Ethan Whisenant

(57) ABSTRACT

The invention provides the use of tetraethylene glycol dimethyl ether for adsorbing nucleic acids to solid phases such as those with silica surfaces. To this end, the invention also provides compositions comprising TDE. Methods are disclosed and claimed to purify nucleic acids from samples, as well as kits useful for performing these methods. Particularly, the invention encompasses methods for the purification of nucleic acids with low molecular weight. The nucleic acids purified by a method of the invention are suited for assays aiming at the detection of a target nucleic acid.

2 Claims, 9 Drawing Sheets

| Sample name | Successful amplification at cycle |
|---|---|
| 1 column Liver | 21.89 |
| 1 column Liver wo. reverse transcriptase | - |
| 2-column Liver | 21.55 |
| 2-column Liver wo. reverse transcriptase | |
| 1-column Kidney | 21.72 |
| 1-column Kidney wo. reverse transcriptase | - |
| 2-column Kidney | 20.89 |
| 2-column Kidney wo. reverse transcriptase | - |
| No template in reverse transcription | - |
| No template in PCR | - |

US 8,124,338 B2

USE OF TDE FOR ISOLATION OF NUCLEIC ACIDS

RELATED APPLICATIONS

This application is a continuation of PCT/EP2007/010793 filed Dec. 11, 2007 and claims priority to EP 06025779.7 filed Dec. 13, 2006.

FIELD OF THE INVENTION

The present invention is directed to the purification of a nucleic acid. Particularly, the invention is directed to methods of adsorbing a nucleic acid present in an aqueous adsorption solution to a solid substrate.

BACKGROUND OF THE INVENTION

Since the structure of DNA was deciphered by Watson & Crick in 1953 (Watson, J. D. and Crick, F. H. C., Nature 171 (1953) 737-738 investigation and handling of nucleic acids becomes an integral part of biochemistry molecular biology. Despite the availability of a number of isolation methods an commercial kits for performing such methods, new developments for fast and easy isolation or purification of nucleic acids with high yield and purity are still of major importance.

Nucleic acids are highly susceptible to enzymatic degradation. In 1968 Cox described the chaotropic agent guanidine HCl as an inhibitor of enzymatic nuclease activity (Cox, R. A., Methods Enzymol. 12B (1968) 120-129). Besides a strong denaturing effect on proteins high concentrations of chaotropic agents also mediate cell lysis. Therefore chaotropic agents, particularly guanidine isothiocyanate, are widely in use for nucleic acid isolation.

A first principle of nucleic acid isolation from a biological sample uses an organic solvent, particularly phenol, for the separation of nucleic acids from, the remaining organic sample components. The phenol extraction is followed by a salt precipitation of the nucleic acid from an aqueous phase (Stallcup, M. R. and Washington, L. D., J. Biol. Chem. 258 (1983) 2802-2807, and Schmitt, M. E. et al., Nucl Acid Res 18 (1990) 3091-3092). Although this method results in nucleic acids with high yield and purity the major drawbacks are the use of poisonous reagents, the time consuming and labor intensive workflow. Due to these disadvantages automation of this isolation principle is not amenable to automation, or only to a very limited extent.

Another principle of nucleic acid isolation makes use of solid inorganic material, particularly silica, to which nucleic acids are adsorbed from an aqueous liquid phase such as a lysate of a biological sample. In 1979 Vogelstein and Gillespie described a method for isolating nucleic acid from agarose gel slices by binding nucleic acids to silica particles in presence of highly concentrated sodium iodide (Vogelstein, B. and Gillespie, D., Proc. Natl. Acad. Sci. USA 76 (1979) 615-619).

In addition it was found that the binding of nucleic acids to the solid phase was increased by the addition of anionic or cationic or neutral detergents, in particular TRITON-X100 (Union Carbide Chemicals & Plastics Technology Corporation), sodium dodecyl sulfate, NP40, and TWEEN 20 (ICI Americas Inc.).

Adsorption of a nucleic acid to the solid phase is usually performed in the presence of a potent denaturant such as a chaotropic agent (Boom, R., et al., J. Clin. Microbiol. 28 (1990) 495-503; U.S. Pat. No. 5,234,809). For the isolation process the biological material is mixed with a solution containing the denaturant. The resulting mix is brought into contact with the solid phase material whereby nucleic acid molecules are bound to the surface of the solid phase. Afterwards the solid material is washed with solutions containing decreasing chaotropic salt concentrations and increasing alcohol concentrations, in particular ethanol, in order to further purify the bound nucleic acids from other organic material and contaminating agents. In the last step the solid material is brought into contact with a low salt solution or water under alkaline pH in order to remove the bound nucleic acid from the solid phase. The complete workflow comprises a sample lysis step, a binding step, one or more washing steps, and an elution (desorption) step.

The solid phase can be arranged in different conformations. In a first design the solid phase is in fleece shape and embedded in a plastic device. An example therefor is a micro spin column (EP 0 738 733). This design is preferentially used in workflows which are performed manually. In a second design magnetic silica particles are used as a solid phase (Bartl, K., et al., Clin. Chem. Lab. Med. 36 (1998) 557-559). This design is preferentially used in automated workflows.

A further improvement of this method was observed when aliphatic alcohol (i.e. ethanol or isopropanol) or polyethylene glycol is added to the solution at the binding step (U.S. Pat. No. 6,383,393).

U.S. Pat. No. 6,905,825 discloses addition of organic solvents to the binding buffer. These organic solvents comprise the aliphatic ethers ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran, and 1,4-dioxane, the aliphatic esters propylene glycol monomethyl ether acetate, and ethyl lactate, and the aliphatic ketones hydroxyacetone, acetone, and methyl ethyl ketone.

US 2005/0079535 discloses the use of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone as well as the use of the cyclic diether dioxane in the binding buffer, in order to adsorb a nucleic acid to a solid phase such as silica.

US 2006/0166368 A1 discloses a liquid solution comprising Tetraethylene glycol dimethyl ether (TED) in a buffer containing (1) a water-miscible organic component such as methanol, ethanol, 1- or 2-propanol, ethylene glycol, propylene glycol, glycerol, acetonitrile, dimethyl sulfoxide, formamide, dimethylformamide, diglyme, triglyme, or tetraglyme, at a concentration of up to 50% (on a volume basis), (2) an acid component such as acetic acid, formic acid, lactic acid, propionic acid, phosphoric acid, trichloroacetic acid, trifluoroacetic acid, citric acid, oxalic acid, or hydrochloric acid, at a concentration of up to 20% (on a volume basis), (3) a buffer such as sodium phosphate, sodium acetate, sodium formate, or sodium citrate, at a pH of from 1 to 6 and a concentration of from 5 to 200 mM, and (4) a detergent such as sodium dodecyl sulfate, TRITON X-100, SB3-10, and TWEEN 20) at a concentration of from 0.005% to 1% (on a weight/volume basis). The liquid solution is used as a solvent of certain dyes which serve as selective labels in protein biochemistry and particularly for methods of protein detection.

The chemical properties of the reagents used in the nucleic acid isolation/purification process determines the quality of the nucleic acid (yield, purity and size) as well as their performance in down-stream workflows, including polymerase or reverse transcriptase based enzymatic reactions (Mullis, K. and Faloona F. A., Methods Enzymol. 155 (1987) 335-350). Furthermore, additional properties of the reagents like toxicity, as well as physical and chemical aspects like flash point and vapor pressure are of major importance.

Recently the analysis of small RNA molecules with 15 to 200 nucleotides gained strong interest. Especially microRNA (miRNA) and small interfering RNA (siRNA), which have a strong effect on the translation of specific messenger RNAs are investigated. Also for other kinds of small RNA like tRNA, 5S and 5.8S rRNA, as well as small nuclear RNA (snRNA) and small nucleolar RNA (snoRNA) involved in mRNA and rRNA processing selective isolation procedures are required.

Methods for isolating such small RNA molecules selectively have been described in US 2005/0059024 by Conrad and in WO 2005/012487 by Madden et al. In order to isolate small RNA molecules in both methods high concentrations of alcohol in the order of 70% is needed to efficiently bind the small RNA to a solid support. This increases the volume of a sample to be analysed considerably. If a sample is to be adsorbed onto a solid support such as a commonly available spin column, the amount of sample that can be applied in one centrifugation run is limited to a small volume. A higher amount of a more diluted sample can be applied only in two consecutive centrifugation steps on the same column, thereby increasing the number of handling steps and processing time. It is therefore another need to improve the binding of small DNA and RNA molecules without the need for diluting the sample with high amounts of alcohol.

In view of the disadvantages of the state of the art it was an object of the present invention to provide an alternative organic compound to promote the adsorption of a nucleic acid to a solid substrate.

The inventors have surprisingly found that adsorption of a nucleic acid to a solid phase is effectively accomplished when tetraethylene glycol dimethyl ether (TDE) is used in the adsorption solution.

SUMMARY OF THE INVENTION

Therefore, a first aspect of the invention is a composition comprising tetraethylene glycol dimethyl ether (TDE; $C_{10}H_{22}O_5$, MW: 178, CAS: 143-24-8), an aqueous buffer, and a chaotropic agent. Another aspect of the invention is the use of TDE for adsorbing a nucleic acid onto a solid phase. Yet, a further aspect of the invention is a method of adsorbing a nucleic acid from a sample onto a solid phase comprising the steps of (a) providing the nucleic acid in a sample, whereby the sample is dissolved in a liquid composition comprising TDE, an aqueous buffer, and a chaotropic agent; followed by (b) providing the solid phase and contacting the liquid composition of step (a) with the solid phase, thereby adsorbing the nucleic acid on the solid phase. Yet, a further aspect of the invention is a method for the purification of a nucleic acid from a lysed sample, comprising the steps of: (a) providing the nucleic acid in a sample, whereby the sample is dissolved in a liquid composition comprising TDE, an aqueous buffer, and a chaotropic agent; followed by (b) providing the solid phase and contacting the liquid composition of step (a) with the solid phase, thereby adsorbing the nucleic acid onto the solid phase; followed by (c) separating the solid phase with the adsorbed nucleic acid from the liquid phase; (d) optionally washing with a washing solution the solid phase with the adsorbed nucleic acid; followed by (e) contacting the solid phase with the adsorbed nucleic acid with a desorption solution which preferably contains solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying the nucleic acid. Yet, a further aspect of the invention is a composition comprising TDE and magnetic particles with a silica surface. Yet, a further aspect of the invention is a method for purifying a nucleic acid with low molecular weight comprising the steps of (a) providing the nucleic acid in a lysed sample, whereby the sample is dissolved in a liquid composition comprising an aqueous buffer, TDE at a concentration between 10% and 75%, measured as volume by volume, a detergent and a chaotropic agent; followed by (b) providing a solid phase and contacting the liquid composition of step (a) with the solid phase; followed by (c) separating the solid phase with the adsorbed nucleic acid from the liquid phase; (d) washing with a washing solution the solid phase of step (c), whereby the washing solution comprises an organic solvent at a concentration of between 40% and about 100%; followed by (e) contacting the solid phase with the adsorbed nucleic acid with an aqueous desorption solution containing solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying the nucleic acid. Yet, a further aspect of the invention is a method comprising the steps of (a) providing the nucleic acid in a lysed sample, whereby the sample is dissolved in a liquid composition comprising an aqueous buffer, TDE at a concentration between 5% and 30%, measured as volume by volume, a detergent and a chaotropic agent; followed by (b) providing a first solid phase, contacting the liquid composition of step (a) with the first solid phase, and separating the liquid phase from the first solid phase; followed by (c) mixing an additional amount of TDE with the liquid phase of step (b), thereby adjusting the concentration of TDE in the liquid phase of step (b) to between 20% and 70%, measured as volume by volume, whereby the initial concentration of TDE in the liquid phase is increased by a factor of 1.3 or more; followed by (d) providing a second solid phase and contacting the liquid composition of step (a) with the second solid phase; followed by (e) washing with a washing solution the second solid phase of step (d), whereby the washing solution comprises an organic solvent at a concentration of between 50% and 100%; followed by (f) contacting the second solid phase of step (e) with an aqueous desorption solution containing solutes in a lower concentration compared to the composition of step (a), thereby desorbing the nucleic acid from the solid phase and dissolving the nucleic acid in the solution; followed by (g) separating the solution with the nucleic acid from the solid phase, thereby purifying the nucleic acid; and optionally (h) precipitating the nucleic acid from the solution of step (f) and isolating the precipitated nucleic acid, thereby further purifying the nucleic acid. Yet, a further aspect of the invention is a kit of parts, comprising packaging material, containers, and (a) TDE, (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, an alkali halogenide, and mixtures thereof; and (c) chromatographic and filtering material comprising a material with a surface capable of interacting with the phosphate residues in the backbone of nucleic acids. Yet, a further aspect of the invention is a kit of parts, comprising packaging material, containers, and (a) a suspension of silica-coated magnetic particles in TDE; and (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, and an alkali halogenide. Yet, a further aspect of the invention is a method for determining the presence of a nucleic acid in a sample, comprising the steps of: (a) forming a composition containing (i) the sample, (ii) an aqueous buffer, (iii) a chaotropic agent, (iv) TDE, whereby the sample is dissolved in the liquid composition; (b) contacting the composition of step (a) with a solid phase, thereby adsorbing the nucleic acid onto the solid phase; (c) separating the solid phase with the adsorbed nucleic acid from the liquid phase; (d) optionally washing with, a washing solution the solid phase with the adsorbed nucleic acid; followed by (e) contacting the solid phase with the adsorbed nucleic acid with an aqueous desorption solution containing solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and (g) detecting in the solution of step (f) the presence of the nucleic acid, thereby determining the presence of the nucleic acid.

Figure 2:
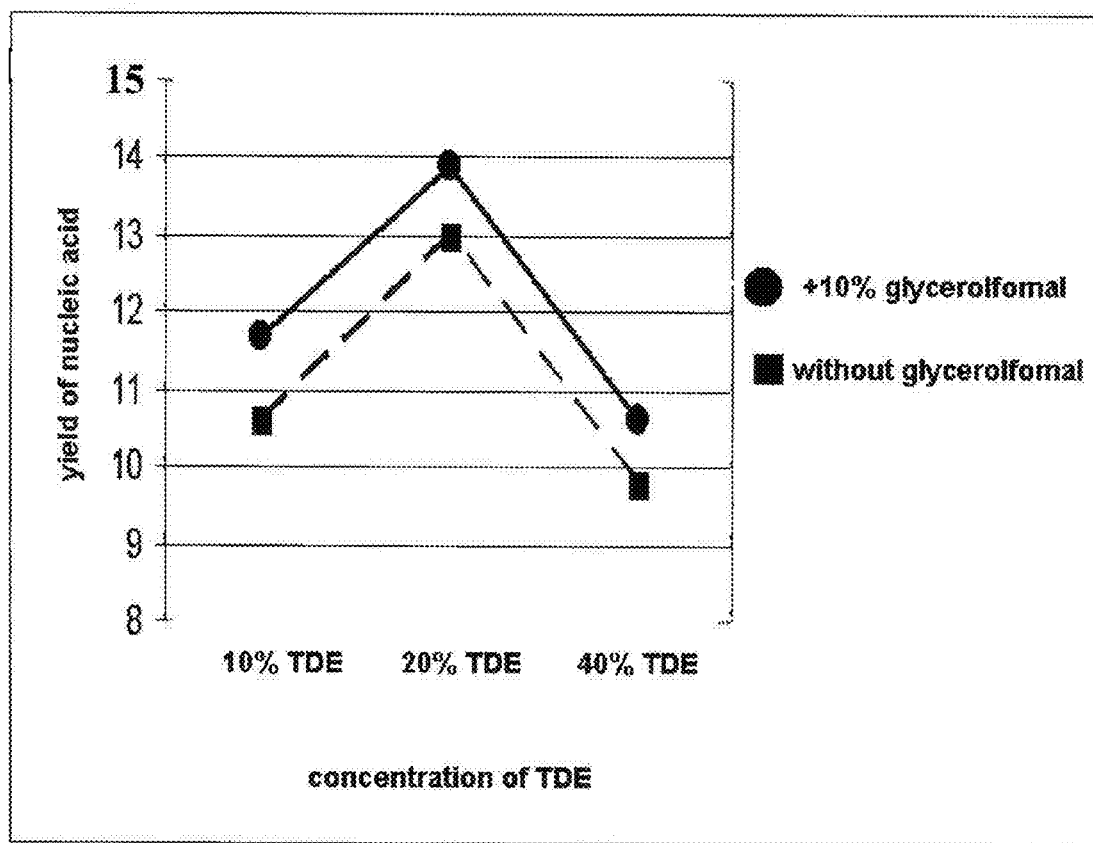

lanes 1 and 18 show the size standard VI (catalogue no. 10236250001, Roche Diagnostics GmbH, Mannheim, Germany)
   lanes 2 and 19 show the size standard II (catalogue no. 10236250001, Roche Diagnostics GmbH, Mannheim, Germany)
   lane 3: tetraethylene glycol dimethyl ether (TDE)
   lane 4: glycerol formal
   lane 5: diethylene glycol diethyl ether
   lane 6: methyl ethyl ketone
   lane 7: propylene glycol dimethylether (dimethoxypropane)
   lane 8: ethylene glycol diethylether (diethoxyethane)
   lane 9: propylene glycol monomethyl ether acetate
   lane 10: tetrahydrofurane
   lane 11: polyethylene glycol 1000
   lane 12: 1,3 dioxolane
   lane 13: hydroxyacetone
   lane 14: ethanol
   lane 15: isopropanol
   lane 16: ethyllactat
   lane 17: acetone FIG. 2 Effect of combinatorial use of TDE and glycerol formal for the purification of total nucleic acids from K562 cells (Example 2).

Figure 3:
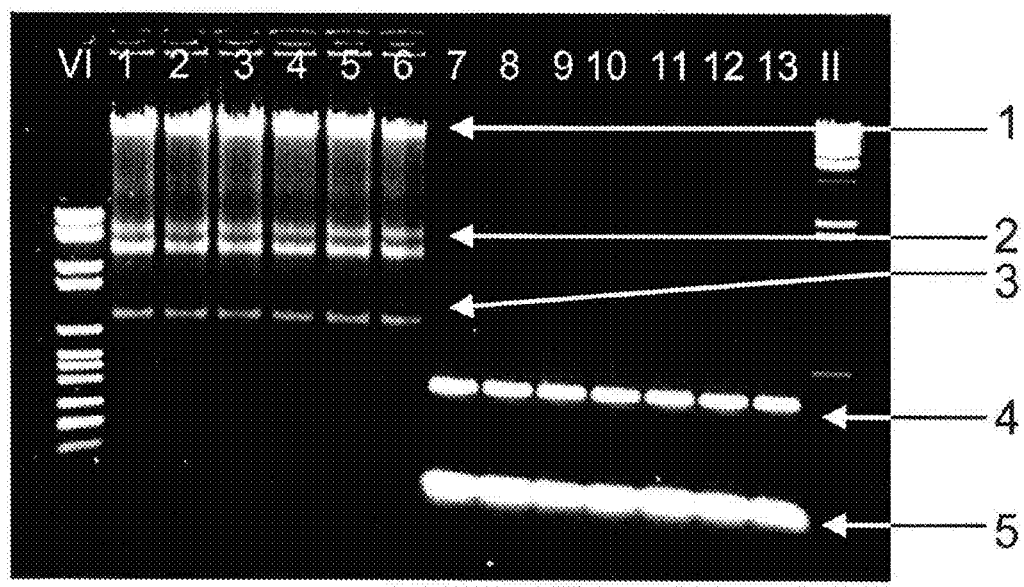

FIG. 3 Nucleic acids isolated/purified with ethanol and TDE as additives in the washing buffer. Following desorption, equal volumes of eluate were subjected to gel electrophoresis in 1% agarose. The gel was stained with ethidium bromide. For further details see Examples 3 (referring to lanes 1-6) and 4 (referring to lanes 7-13).

lane VI: DNA size standard VI (catalogue no. 10236250001, Roche Diagnostics. GmbH, Mannheim, Germany)
   lane 1-3: nucleic acid preparation from k562 cells using ethanol in washing buffers
   lanes 4-6: nucleic acid preparation from k562 cells using TDE in washing buffers
   lane 7-9: recovered DNA fragments using ethanol in washing buffers
   lane 10-12: recovered DNA fragments using TDE in washing buffers
   lane 13: DNA fragments, untreated solution
   lane II: DNA size standard II (catalogue no. 10236250001, Roche Diagnostics GmbH, Mannheim, Germany)

Figure 4:
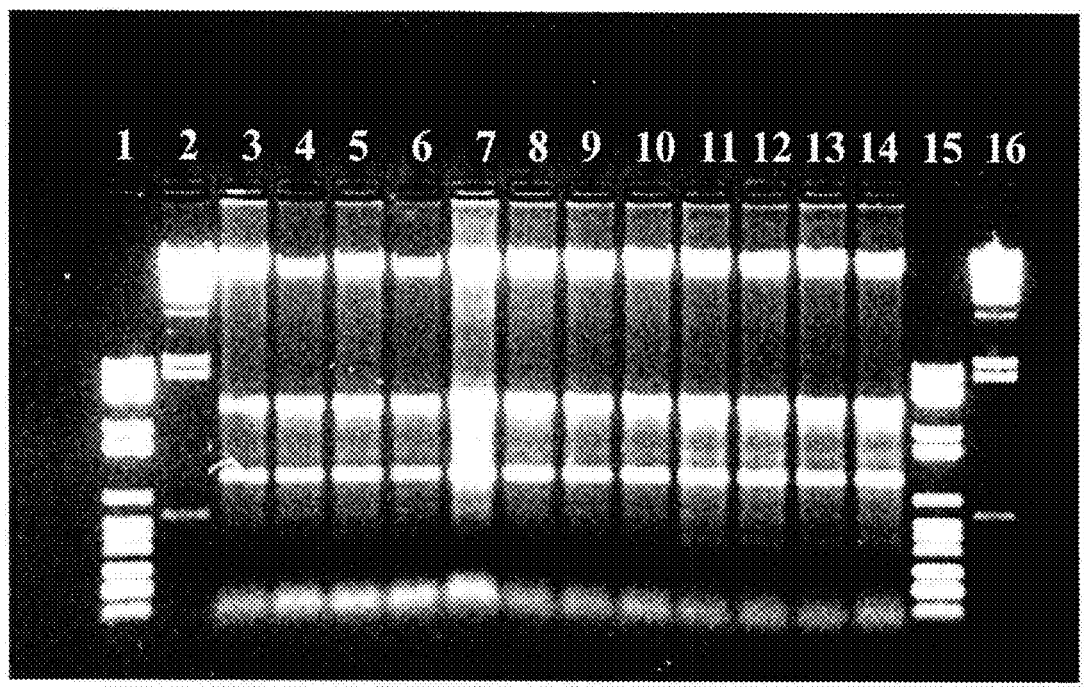

FIG. 4 An eluate aliquot containing 500 ng of isolated nucleic acids was subjected to electrophoresis in an 1% agarose gel which was stained afterwards with ethidium bromide.

lane 1: size standard VI (catalogue no. 11062590001, Roche Diagnostics GmbH, Mannheim, Germany)
   lane 2: size standard II (catalogue no. 10236250001, Roche Diagnostics GmbH, Mannheim, Germany)
   lanes 3-6: magnetic particles supplied as suspension in TDE
   lanes 7-10: magnetic particles supplied as suspension in diethyleneglycol diethyl ether
   lanes 11-14 magnetic particles supplied as suspension in magnetic particles supplied as suspension in isopropanol
   lane 15: size standard VI (catalogue no. 11062590001, Roche Diagnostics GmbH, Mannheim, Germany)
   lane 16: size standard II (catalogue no. 10236250001, Roche Diagnostics GmbH, Mannheim, Germany)

Figure 5:
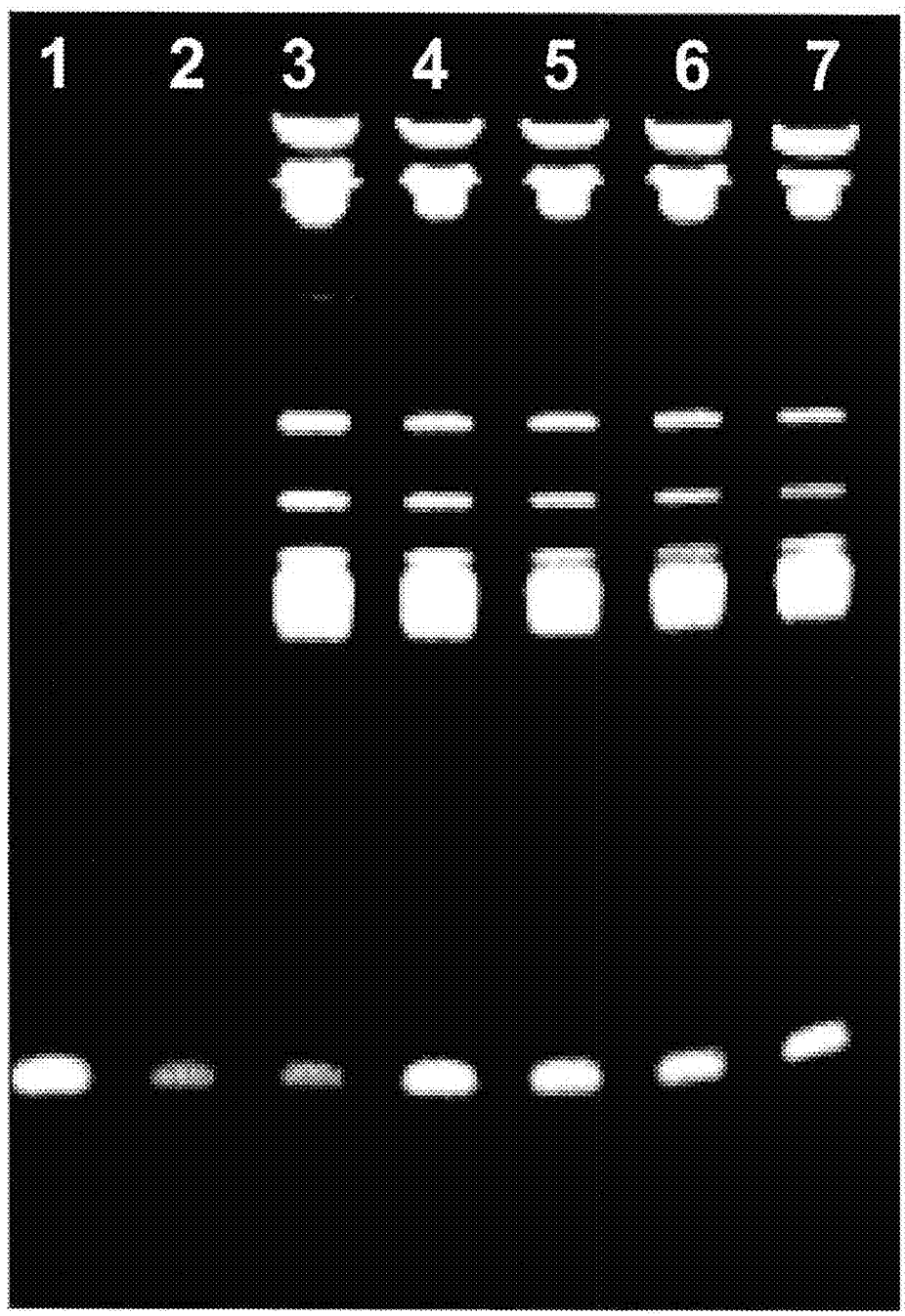

FIG. 5 Binding of low molecular weight nucleic acid molecules of various sizes using different TDE concentrations in the binding step.

lane 1: 100 ng pre-purified miRNA16, untreated
   lane 2: 50 ng pre-purified miRNA16, untreated
   lane 3: adsorption in TDE 35% [v/v]
   lane 4: adsorption in TDE 40% [v/v]
   lane 5: adsorption in TDE 45% [v/v]
   lane 6: adsorption in TDE 50% [v/v]
   lane 7: adsorption in TDE 55% [v/v]

Figure 6:
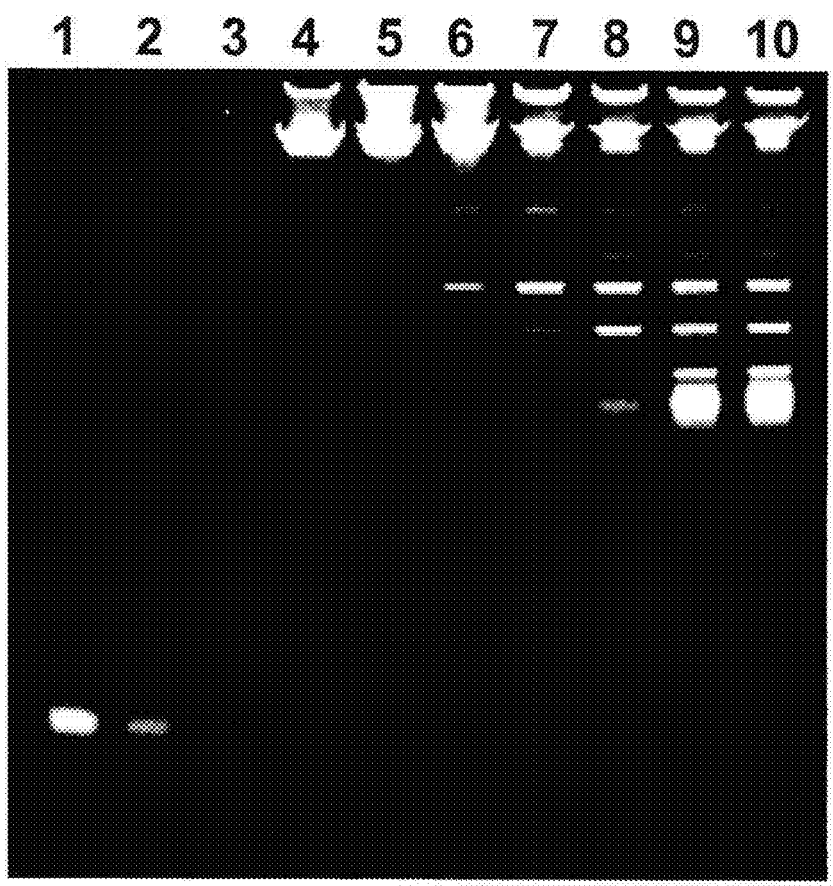
Figure 6:
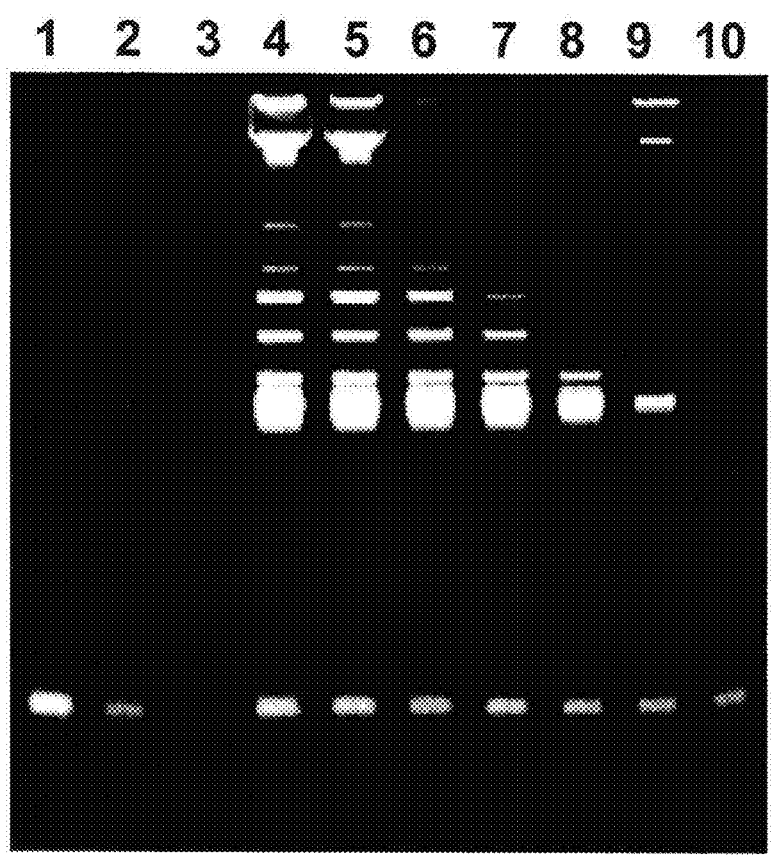

FIG. 6 A Purification of low molecular weight nucleic acid molecules using two consecutive, separations with spin columns: Different concentrations of TDE (as indicated below) were used for adsorption to the first column. Lanes 4-10 indicate the nucleic acids separated from the adsorption solution with the first column and eluted therefrom.

lane 1: 100 ng pre-purified miRNA16, untreated
   lane 2: 50 ng pre-purified miRNA16, untreated
   lane 3: 25 ng pre-purified miRNA16, untreated
   lane 4: 0% [v/v] TDE
   lane 5: 5% [v/v] TDE
   lane 6: 10% [v/v] TDE
   lane 7: 15% [v/v] TDE
   lane 8: 20% [v/v] TDE
   lane 9: 25% [v/v] TDE
   lane 10: 30% [v/v] TDE FIG. 6 B Low molecular weight nucleic acid molecules were adsorbed to a second spin column from the flow-through of the first spin column using a final TDE concentration of 40% [v/v] in each case. Lanes 4-10 indicate the purified nucleic acids of low molecular weight which were eluted from the respective second column subsequent to the separation with a given TDE concentration for the first column.

lane 1: 100 ng miRNA16 lane 2: 50 ng miRNA16 lane 3: 25 ng miRNA16 lane 4: eluate from second column after adsorption with 0% [v/v] TDE on the first column lane 5: eluate from second column after adsorption with 5% [v/v] TDE on the first column lane 6: eluate from second column after adsorption with 10% [v/v] TDE on the first column lane 7: eluate from second column after adsorption with 15% [v/v] TDE on the first column lane 8: eluate from second column after adsorption with 20% [v/v] TDE on the first column lane 9: eluate from second column after adsorption with 25% [v/v] TDE on the first column lane 10: eluate from second column after adsorption with 30% [v/v] TDE on the first column FIG. 7 Detection of mir17a in isolates from mouse tissues using a specific RT-PCR assay and Light Cycler amplification.

Total Nucleic acids and small nucleic acid molecules of sizes smaller than 150 nucleotides (i.e. microRNA) were isolated from liver and kidney tissue with the one column or the two column protocol, respectively, and detected using a Q-RT-PCR (quantitative PCR following reverse transcription). The table shows at which amplification cycle the miRNA 17a was detected.

Figure 8:
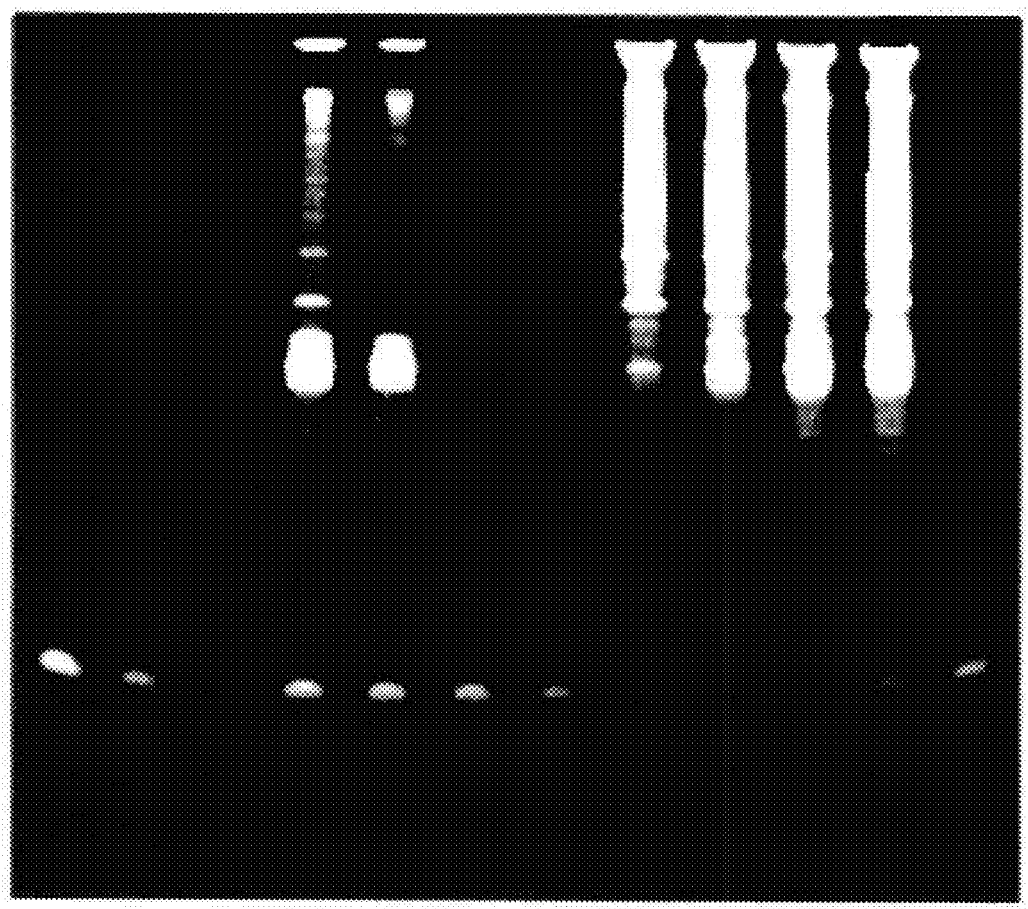

FIG. 8 Optimizing binding enhancer concentration on column 1 for miRNA-purification from tissue Different concentrations of TDE (as indicated below) were used for adsorption to the first column. Lanes 8-11 indicate the nucleic acids separated from the adsorption solution with the first column at the indicated TDE concentrations and eluted therefrom. Small nucleic acid molecules were adsorbed to a second spin column from the flow-through of the first spin column using a final. TDE concentration of 40% [v/v] in each case. Lanes 4-7 indicate the purified nucleic acids of low molecular weight which were eluted from the respective second column subsequent to the separation with a given TDE concentration for the first column.

lane 1: 100 ng synthetic miRNA16 lane 2: 50 ng synthetic miRNA16 lane 3: 25 ng synthetic miRNA16 lane 4: Eluate from second column after adsorption with 10% [v/v] TDE on the first column lane 5: Eluate from second column after adsorption with 15% [v/v] TDE on the first column lane 6: Eluate from second column after adsorption with 20% [v/v] TDE on the first column lane 7: Eluate from second column after adsorption with 25% [v/v] TDE on the first column lane 8: 10% [v/v] TDE lane 9: 15% [v/v] TDE lane 10: 20% [v/v] TDE lane 11: 25% [v/v] TDE lane 12: 50 ng synthetic miRNA16

DETAILED DESCRIPTION OF THE INVENTION

The present invention provides new compositions and methods for the purification of nucleic acids. Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

Further, it is understood that the term "about" in combination with a numerical value n indicates a value x in the interval given by the numerical value±5% of the value, i.e. $n-0.05*n \leq x \leq n+0.05*n$. In case the term "about" in combination with a numerical value n describes a preferred embodiment of the invention, the value of n is most preferred, if not indicated otherwise.

The term "water-miscible" indicates that at room temperature and normal atmospheric pressure a water-miscible compound can be dissolved in water at a ratio equal or greater than 1% (percent) volume by volume, to form a homogeneous aqueous liquid phase. An unlimited water-miscible compound, when mixed with water, forms a homogeneous liquid phase at any water/compound ratio. In case the solubility of the water-miscible compound is limited in water, the compound may form a separate phase in addition to the aqueous phase. The compound may also form an emulsion, especially in the presence of a surfactant.

A compound or a composition is a "liquid" if at room temperature and normal atmospheric pressure the compound is in the "liquid" state and forms a liquid phase.

The terms "aqueous", "aqueous" phase and "aqueous" solution describe a liquid phase of which the solvent portion comprises water. However, other solvents such as a water-miscible organic solvent can be present in the solvent portion, too. In view of the presence of other solvents a solution is considered "aqueous" when between 30% and 100%, measured as volume by volume [v/v], of the solvent portion is water.

A "chaotropic agent" is a compound which weakens hydrophobic interactions of the components in an aqueous solution. Certain ions in water will tend to increase hydrophobic interactions, while other ions will decrease hydrophobic interactions. Which ions have a tendency to which effect is described by what is called a Hofmeister series. The series is as follows:

Cations:
$NH_4^+ > Rb^+ > K^+ > Na^+ > Cs^+ > Li^+ > Mg^{2+} > Ca^{2+} > Ba^{2+} >$ guanidine Anions:
$PO_4^{3-} > SO_4^{2-} > HPO_4^{2-} >$ acetate$>$citrate$>$tartrate$>Cl^- > Br^- > NO_3^- > ClO_3^- > ClO_4^- > I^- > SCN^-$ Ions on the left are said to be "kosmotropic" and increase the strength of hydrophobic interactions and thus will precipitate or "salt out" proteins at a high concentrations. Ions on the right are "chaotropic" and tend to weaken hydrophobic interactions. The Hofmeister series explains why a guanidine salt is a protein denaturant. It weakens hydrophobic interactions causing proteins to denature. In addition to the above, there are also chaotropic compounds which are non-ionic. An example therefor is urea.

In the present document it is understood that the term "a nucleic acid" denotes at least one nucleic acid. Furthermore, the term "a nucleic acid" also may indicate a mixture of nucleic acids. The term "nucleic acid" encompasses RNA, DNA, or both.

The term "solid phase" to which a nucleic acid is adsorbed is understood as being a substrate which is insoluble in the compositions according to the invention. A preferred solid phase is a substrate with a surface capable of interacting with the phosphate groups of the backbone of nucleic acids. The solid phase may be in the form of porous or non-porous particles, powdered particles, or fibers. A solid phase consisting of fleece material which comprises a plurality of non-woven fibers is also encompassed. Preferred solid phases consist of glass. Preferred solid phases are porous or non-porous mineral substrates such as silica, quartz, celites or other materials with oxidic surfaces (including, e.g. zirconium oxide, aluminum oxide, and other metal oxides) or mixtures thereof. Also, the term "solid phase" encompasses magnetically attractable particles coated with silica, glass, quartz, or celites. Further, it is understood that a substrate in the form of "powder" or "powdered" material refers to finely divided material which, when dispersed in a liquid composition according to the invention, produces a suspension. The term "powder" or "powdered" material is intended to include tablets, in which the powdered material has been aggregated, but still yields a suspension when combined with a liquid phase.

The term "silica" as used within this application denotes materials which are mainly build up of silicon and oxygen. These materials comprise silica, silicon dioxide, silica gel, fumed silica gel, diatomaceous earth, celite, talc, quartz, glass, glass particles including all different shapes of these materials. Glass particles, for example, may comprise particles of crystalline silica, soda-lime glasses, borosilicate glasses, and fibrous, non-woven glass.

The term "magnetic particle" denotes a particle with paramagnetic or superparamagnetic properties. That is to say, the particle is magnetically displaceable but does not retain any magnetisation in the absence of an externally applied magnetic field.

The term "sample" (or "sample material") as used herein refers to a complex sample, more preferred a biological sample. A complex sample may contain a plurality of organic and inorganic compounds which are desired to be separated from the nucleic acid. The term "sample" also encompasses an aqueous solution containing nucleic acids derived from other origins, e.g. from chemical or enzymatic reaction mixtures, or from a previous purification of biological sample material. The term biological sample, from which nucleic acids are purified, encompasses samples comprising viruses or bacterial cells, as well as isolated cells from multicellular organisms such as human and animal cells as well as tissues and cell cultures. Particularly, the sample can contain leucocytes, and other immunologically active cells, chemical compounds with a low and/or a high molecular weight such as haptens, antigens, antibodies and nucleic acids. The sample can be whole blood, blood serum, blood plasma, cerebral fluid, sputum, stool, biopsy specimens, bone marrow, oral rinses, tissues, urine or mixtures thereof. The present invention also encompasses biological samples such as a fluid from the human or animal body; preferably the biological sample is blood, blood plasma, blood serum or urine. The blood plasma is preferably EDTA, heparin or citrate blood plasma. In an embodiment of the invention the biological sample comprises bacterial cells, eukaryotic cells, viruses or mixtures thereof. A biological sample as exemplified above, preferably in a processed form such as a lysate, can be part of the composition from which the (target) nucleic acid is adsorbed to the substrate. Also encompassed by the term "biological sample" are cells from plants, and fungi as well as single cell organisms.

A preferred sample according to the invention is a lysate. A "lysate" or a "lysed sample" can be obtained from a complex sample and/or biological sample material comprising tissue, cells, bacteria or viruses, whereby the structural integrity of the material is disrupted. To release the contents of cells, tissue or, more generally, from the particles which make up a biological sample, the material may be treated with enzymes or with chemicals to dissolve, degrade or denature the cellular walls and cellular membranes of such organisms. This process is encompassed by the term "lysis". It is common to use chaotropic agents such as a guanidine salt and/or anionic, cationic, zwitterionic or non-ionic detergent when nucleic acids are set free in the lysis process. It is also an advantage to use proteases which rapidly degrade enzymes with nucleolytic activity and other unwanted proteins. In case there remains particulate, i.e. undissolved matter of the sample material following the lysis process, the particulate matter is usually separated from the lysate to result in a cleared lysate. This can be done, e.g., by way of filtering or centrifugation. In such a case the cleared lysate is processed further, e.g. by a method according to the invention. Thus, the term "lysed sample" encompasses a cleared lysate.

Nucleic acids which are set free can be purified by way of binding (adsorbing) to a solid phase, washing said solid phase with the bound nucleic acids and releasing, i.e. desorbing said nucleic acids from said mineral support.

Hazardous substances used as binding enhancers often bear environmental risks and cause high costs for waste management. Their use can be restricted based on the required technical and/or operational safety measures to be taken. The hazardous potential of buffers used in the isolation/purification of nucleic acids is chiefly influenced by the choice of the organic compound which promotes adsorption of the nucleic acid to the solid phase. With respect to the environmental burden it is desired to reduce the use of toxic or harmful agents as far as possible. Also, the flash point of a flammable organic compound, that is the lowest temperature at which it can form an ignitable mixture with oxygen, is desired to be high. This parameter particularly influences the costs of production of kits for nucleic acid purification. An organic compound with a flash point below room temperature has to be handled in specially equipped production facilities which prevent the development of explosive vapor. In addition, restrictions apply to the transport of such organic compounds. A low flash point is usually correlated with a high vapor pressure. As a consequence, certain organic compounds, particularly lower alcohols, tend to evaporate from solutions and therefore lead to variations in concentration over time. This effect also influences stability during storage as well as the handling of liquids with a high vapor pressure in an automated pipetting instrument. Avoiding substances with low flash points and a tendency to evaporate in the isolation/purification process would make the production of solutions for the purification of nucleic acids simpler and more economical. In addition, compounds with a low vapor pressure are desired as they increase the utility of nucleic acid isolation kits by eliminating a major source of pipetting error, thereby increasing the reliability of such kits.

The inventors have surprisingly found that adsorption of a nucleic acid to a solid phase is effectively accomplished when tetraethylene glycol dimethyl ether (TDE; $C_{10}H_{22}O_5$, MW: 178, CAS: 143-24-8) is used in the adsorption solution. TDE, like butyl diglyme, is a very safe and effective solvent for a wide ranges of uses. TDE boils at 275° C. and has a flash point of 141° C. TDE is completely water soluble. Table 1 provides a comparison of TDE with some organic compounds which can also be used as additives for adsorbing a nucleic acid to a solid phase.

TABLE 1

| | flash point | vapor pressure | hazard classification |
|---|---|---|---|
| Aliphatic Ether | | | |
| Ethylene Glycol Dimethyl Ether | −2° C. | 48 | F, T |
| Ethylene Glycol Diethyl Ether | 35° C. | 9.4 | Xi |
| Propylene Glycol Dimethyl Ether | 1° C. | 40 | F |
| Diethylene Glycol Dimethyl Ether | 56° C. | 3 | T |
| Diethylene Glycol Diethyl Ether | 82° C. | 0.5 | Xi |
| Tetrahydrofuran | −24° C. | 143 | F, Xi |
| 1,4-Dioxane | 12° C. | 27 | F, Xn |
| Tetraethylene Glycol Dimethyl Ether (TDE) | 141° C. | <0.01 | |
| Aliphatic Polyether | | | |
| Polyethylen Glycol 1000 | n/a | n/a | |
| Aliphatic Ester | | | |
| Propylene Glycol Monomethyl Ether Acetate | 43° C. | 3.7 | Xi |
| Ethyl Lactate | 52° C. | 2 | Xi |
| Acetal | | | |
| Glycerolformal | 93° C. | n/a | |
| 1,3 Dioxolane | −3° C. | 70 | F, Xi |
| 1,3 Dioxane | 5° C. | n/a | F, Xn |
| Aliphatic Ketone | | | |
| Acetone | −15° C. | 184 | F, Xi |
| Metyl Ethyl Ketone | −7° C. | 71 | F, Xi |
| Hydroxyacetone | 56° C. | 5.6 | |
| Aliphatic Alcohol | | | |
| Isopropanol | 12° C. | 33 | F, Xi |
| Ethanol | 13° C. | 44.6 | F |

Hazard classifications are given as generally known: "F" (=flammable), T (=toxic), Xi (=irritant)

Flash point, vapor pressure as well as information about hazard classification was obtained from the material safety data available from the suppliers' internet pages (Sigma Aldrich).

By virtue of its high flash point the use of TDE for adsorbing a nucleic acid to a solid support reduces a great deal of hazardous potential. At the same time, a superior performance in the nucleic acid isolation process was observed compared with additives known so far. The present invention increases the convenience and reduces the costs for nucleic acid isolation/purification for the producer of nucleic acid isolation kits as well as for the user of such kits. The reduced use of toxic or harmful substances lowers the environmental risks. The reduction or even replacement of flammable substances lowers production and shipping costs. Increased convenience is achieved due to the fact that the end user of a kit can be provided with ready-made kits without the need to add components (e.g. ethanol) to a buffer component of the kit. Also, lesser evaporation in TDE-containing buffers is observed, thereby making automated liquid handling more reliable.

According to the invention, the binding of a nucleic acid to a solid phase can be performed with a composition comprising tetraethylene glycol dimethyl ether (TDE), an aqueous buffer, and a chaotropic agent with the exception of acetate at a pH of from 1 to 6 and a concentration of from 5 to 200 mM.

According to the invention, the preferred concentration of TDE in the composition is between 10% and 75%, measured as volume by volume, also referred to as [v/v]. Even more preferred, the concentration of TDE is between 20% [v/v] and 55% [v/v]. Even more preferred, the concentration of TDE is between 30% [v/v] and 45% [v/v]. Most preferred, the TDE concentration in the composition is about 40% [v/v].

According to the invention, addition of a further water-miscible liquid organic solvent as an additive has proved to be advantageous for the process of adsorbing the nucleic acid to the solid phase. A preferred additive is a C1-C5 aliphatic alcohol. A very much preferred aliphatic alcohol is ethanol or isopropanol. However, such compounds are flammable and vaporize rather easily. Thus, more preferred is a liquid water-miscible acetal or ketal which have a reduced tendency to evaporate. Such carbonyl derivatives are characterized by their stability and lack of reactivity in neutral to strongly basic environments. This is particularly the case for cyclic acetals or ketals which are formed by reaction of diols with aldehydes or ketones, respectively. Thus, very much preferred, the composition according to the invention additionally comprises a compound selected from the group consisting of 1,3-dioxolan, 1,3-dioxan, 5-hydroxy-1,3-dioxane and 4-hydroxymethyl-1,3-dioxolane, and a mixture thereof. A mixture of 5-hydroxy-1,3-dioxane and 4-hydroxymethyl-1,3-dioxolane is also known as "glycerol formal". Most preferred, the composition according to the invention additionally comprises glycerol formal. However, one or more of the above acetals can also be used as a preferred additive in a composition comprising magnetic particles or in a washing buffer (see below).

The preferred pH value of the composition according to the invention is between 4 and 7.5. Even more preferred, the pH value is between 5.5 and 7.5. It is obvious for the artisan to produce suitable aqueous buffered solutions. In order to stabilize the pH value, a buffer is present in the composition according to the invention. Buffer systems which suitable for molecular biology purposes may be found e.g. in Sambrook, Fritsch & Maniatis, Molecular Cloning, A Laboratory Manual, 3rd edition, CSHL Press, 2001. Preferred buffer substances are acetic acid, citric acid, phosphoric acid, N-(Carbamoylmethyl)-2-aminoethanesulfonic acid (ACES), N-(2-Acetamido)iminodiacetic acid (ADA), N,N-Bis(2-hydroxyethyl)-2-aminoethanesulfonic acid (BES), Tris-(hydroxymethyl)-aminomethane (TRIS), 2-Bis(2-hydroxyethyl)amino-2-(hydroxymethyl)-1,3-propanediol (BIS-TRIS), N-(2-Hydroxyethyl)piperazine-N'-(2-ethanesulfonic acid) (HEPES), 2-(N-Morpholino)ethanesulfonic acid (MES), 3-(N-Morpholino)propanesulfonic acid (MOPS), 3-(N-Morpholinyl)-2-hydroxypropanesulfonic acid (MOPSO), piperazine-N,N'-bis(2-ethanesulfonic acid) (PIPES), salts thereof, or other suitable substances.

In detail, the procedure for binding a nucleic acid (also referred to as target nucleic acid) to a solid phase such as, e.g., glass particles can be described as follows. It is preferably performed in the presence of a chaotropic agent with a concentration of between 0.5 M and 10 M, and preferably between 1 M and 5 M. Most preferred, the concentration of the chaotropic agent is between 2 M and 4 M. A preferred chaotropic agent is selected from the group consisting of a guanidine salt such as guanidine hydrochloride, guanidine thiocyanate and guanidine isothiocyanate, furthermore urea, an alkali acetate salt such as sodium acetate and potassium acetate, furthermore an alkali perchlorate, an alkali iodide, lithium chloride, potassium chloride, and sodium chloride. Mixtures comprising one or more of the listed agents are also possible.

When lysing a biological sample in order to set free the nucleic acids or when binding the nucleic acid to the solid phase it is further preferred to use a detergent in the procedures, that is to say an anionic, cationic, zwitterionic or non-ionic detergent. Such detergents are well known to the person skilled in the art. Generally, a "detergent" is a surface active agent, also known as a surfactant. A detergent is capable of lowering the surface tension of the medium in which it is dissolved, and/or the interfacial tension with other phases, and, accordingly, is positively adsorbed at the liquid/vapor and/or at other interfaces. Thus, detergents are amphipathic molecules with polar (water soluble) and nonpolar (hydrophobic) domains. They are capable of binding to hydrophobic molecules or molecular domains to confer water solubility. Depending on its ionic characteristics, a detergent can be categorized as an ionic detergent, a non-ionic detergent, and a zwitterionic detergent. Ionic detergents can be further classified into either anionic detergents such as SDS (sodium dodecyl sulfate) LIDS (lithium dodecyl sulfate), sodium lauroyl sarcosine, 1-octanesulfonic acid, cholic acid, or deoxycholic acid, and cationic detergents such as cetyl trimethylammonium bromide (CTAB), trimethyl(tetradecyl)ammoniumbromide, lauryl trimethylammonium chloride (LTAB), lauryl trimethylammonium schloride (LTAC) or stearyl trimethylammonium chloride (STAC). Thus, these are usually highly protein denaturant. Non-ionic detergents such as Nonidet P40, TWEEN 20, TRITON X-100, BRIJ 35 P (ICI Americas Inc.), saponin, N,N-dimethyldodecylammine-N-oxide, N,N-dimethyldodecylamine-N oxide, or nonaethylene glycol monododecyl ether are usually less protein denaturant. This is also true for zwitterionic detergents such as 3-(N,N-dimethylpalmitylammonio) propanesulfonate, 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO) or Sulphobetaine 14. Zwitterionic compounds, also known as zwitterions, inner salts or dipolar ions are neutral compounds having formal unit electrical charges of opposite sign.

The composition according to the invention may thus also comprise a detergent. It is preferred that the composition comprises an anionic, cationic, zwitterionic or non-ionic detergent. It is even more preferred that the detergent in the composition is selected from the group consisting of Sodium dodecyl sulfate, Lithium dodecyl sulfate, Cetyltrimethylammoniumbromide, Deoxycholic acid, Sodium lauroyl sarcosine, TRITON-X100, TWEEN 20, Octyl beta-D-glucoside, Nonidet P40, BRIJ 35 P or Sulphobetaine 14. However, other detergents are possible.

Moreover, the composition may contain a protease. Generally, when using the combination of a chaotropic agent, a detergent and a protease for lysing a biological sample, the skilled artisan selects e chaotropic agent and the detergent and their concentrations in the composition according to the invention on the basis that proteolytic activity is preserved in the composition.

The composition according to the invention which additionally contains a nucleic acid is also referred to as an "adsorption solution" because the composition provides the conditions necessary for adsorbing the nucleic acid to a solid phase. Thus, another aspect of the invention is the use of TDE for adsorbing a nucleic acid onto a solid phase. Yet, a further aspect of the invention is a method of using TDE and a nucleic acid in a sample comprising the steps of (a) providing the nucleic acid in a sample, whereby the sample is dissolved in a liquid composition comprising TDE, an aqueous buffer, and a chaotropic agent; followed by (b) providing the solid phase and contacting the liquid composition of step (a) with the solid phase, thereby adsorbing the nucleic acid on the solid phase. Preferably, the sample has been treated in order to obtain a lysed sample.

To bring the sample in contact with the solid phase, i.e. the material with an affinity to nucleic acids, the sample is mixed with the material and incubated for a period of time sufficient for the binding to occur. Experts are usually familiar with the duration of the incubation step. This step can be optimized by determining the quantity of immobilized biological material on the surface at different points in time. Incubation times of between 1 second (s) and 30 minutes (min) can be appropriate for nucleic acids. After incubation, the solid phase with the adsorbed nucleic acid(s) is separated from the liquid. This may be achieved in general by gravity in the case a suspension of a pulverized solid phase such as glass powder is used. In the convenient case of nucleic acids bound to magnetic glass particles separation can be achieved by immobilizing the magnetic particles with a magnetic field and removing the liquid phase. For instance, the magnetic particles can be pulled to the wall of the vessel in which incubation was performed. The liquid containing the sample contents that are not bound to the magnetic particles can then be removed. The removal procedure used depends on the type of vessel in which incubation was performed. Suitable steps include removing the liquid via pipetting or aspiration. Another example is binding the nucleic acid in the adsorption solution to a glass fleece. Commercial kits often provide such a fleece at the bottom of a column. The adsorption solution containing the nucleic acid is transferred to the column and passed through the fleece by applying force. The term "force" includes gravitational force and, preferred, centrifugal force. Very much preferred is the "spin column" procedure wherein the adsorption solution is passed through the filter due to force being applied by way of centrifugation. Other ways to pass the adsorption solution through the fleece include the application of pressure or suction.

According to the invention, a preferred solid phase comprises a porous or non-porous silica substrate. More preferred, the solid phase comprises a substrate selected from the group consisting of glass fibers and quartz fibers. Also very much preferred, the solid phase comprises magnetic particles with a silica surface. Magnetizable particulate adsorbents are a very much preferred solid phase because they are suitable for automatic sample preparation. Ferrimagnetic and ferromagnetic as well as superparamagnetic particles are used for this purpose. Very much preferred magnetic glass particles are those described in WO 01/37291. It is very convenient to provide the magnetic particles as a suspension in an aqueous solution of TDE. Also preferred, the magnetic particles are provided as a suspension in a solution comprising a water-miscible cyclic acetal and TDE. The solution may additionally comprise water. Therefore, another aspect of the invention is a composition comprising TDE and magnetic particles with a silica surface liquid composition comprising TDE and magnetic particles with a silica surface. Preferably the particles are provided as powdered material. The magnetic glass particles used in the present invention may be provided in different formulations. It is possible to provide them in the form of a tablet, as a powder or as a suspension which is preferred. Preferably, these suspensions contain between 5 to 60 mg/ml magnetic glass particles. Also preferred, the silica-containing material is suspended in an aqueous buffered solution which may optionally contain a chaotropic agent in a concentration of between 1 M and 10 M, and preferably between 2 M and 6 M.

Yet, a further aspect of the invention is a method for the purification of a nucleic acid from a lysed sample, comprising the steps of: (a) providing the nucleic acid in a sample, whereby the sample is dissolved in a liquid composition comprising TDE, an aqueous buffer, and a chaotropic agent; followed by (b) providing the solid phase and contacting the liquid composition of step (a) with the solid phase, thereby adsorbing the nucleic acid onto the solid phase; followed by (c) separating the solid phase with the adsorbed nucleic acid from the liquid phase; (d) optionally washing with a washing solution the solid phase with the adsorbed nucleic acid; followed by (e) contacting the solid phase with the adsorbed nucleic acid with a desorption solution which preferably contains solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying or concentrating the nucleic acid. The purification effect results from the behavior of DNA or RNA to bind to material with a glass surface under the conditions provided by the composition of the invention in the adsorption solution containing the nucleic acid to be purified.

The washing step may not always be necessary and therefore represents a non-mandatory option. Performing the washing step is opted for by the skilled person depending on the sample material from which the nucleic acid is to be purified. The purpose of the washing step(s) is to remove contaminants, i.e. undesired components of the sample material from the adsorbed nucleic acid. A washing solution is used that does not cause nucleic acid(s) to be released from the surface of the solid phase but that washes away the undesired contaminants as thoroughly as possible.

A washing step is preferably performed by incubating the material with the adsorbed nucleic acid(s) with the washing solution. The solid phase material is preferably resuspended during this step. Also preferred, in case the material is a glass fleece or a packing in a column, the washing step takes place by rinsing the column with the washing solution. Preferably, the washing solution is passed through the column by applying pressure, suction, centrifugal force or gravitational force. The contaminated washing solution is preferably removed just as in the step described above for binding the nucleic acid to the solid phase. After the last washing step, the material can be dried briefly in a vacuum, or the fluid can be allowed to evaporate. Prior to desorption, a pretreatment step using acetone may also be performed.

Preferably, the washing solution contains an organic compound selected from the group consisting of TDE, a C1-C5 aliphatic alcohol and a liquid water-miscible cyclic acetal, furthermore a chaotropic agent at a concentration between 0.5 M and 10 M, whereby the pH value of the washing solution is between pH 4 and pH 7.5. The preferred concentration of the organic compound in the washing solution is between 10% and 90% [v/v]. A very much preferred aliphatic alcohol is ethanol or isopropanol.

Under the conditions provided by the washing solution preferably greater than 40%, more preferred greater than 50%, more preferred greater than 70%, more preferred greater than 80%, even more preferred greater than 90%, even more preferred greater than 95%, even more preferred greater than 99% of the nucleic acids remain adsorbed to the solid phase.

Using a narrow concentration range for TDE the inventors surprisingly found a way how to isolate small nucleic acids such as miRNA, siRNA, etc. Thus, another aspect of the invention is directed to a method of using TDE and a nucleic acid of low molecular weight in a sample. The invention encompasses a method for purifying a nucleic acid with low molecular weight comprising the steps of (a) providing the nucleic acid in a lysed sample, whereby the sample is dissolved in a liquid composition comprising an aqueous buffer, TDE at a concentration between 10% and 75%, measured as volume by volume, a detergent and a chaotropic agent; followed by (b) providing a solid phase and contacting the liquid composition of step (a) with the solid phase; followed by (c) separating the solid phase with the adsorbed nucleic acid from the liquid phase; (d) washing with a washing solution the solid phase of step (c), whereby the washing solution comprises an organic solvent at a concentration of between 40% and about 100%; followed by (e) contacting the solid phase with the adsorbed nucleic acid with an aqueous desorption solution containing solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying or concentrating the nucleic acid.

The liquid composition of step (a) may additionally comprise a detergent, preferably a non-ionic detergent or sodium lauroyl sarcosine. Also preferred, in step (a) the concentration of TDE in the composition is between 30% and 50%, and most preferred about 40%, measured as volume by volume.

Very much preferred, the chaotropic agent in the composition of step (a) is in a concentration between 0.5 M and 10 M. Also preferred, the chaotropic agent comprises guanidine isothiocyanate. Furthermore, the composition of step (a) including the sample is preferably buffered to a pH between 4.0 and 7.0, very much preferred a pH between 4.5 and 6.5, and also very much preferred a pH between 5.5 and 7.

Alternatively, a nucleic acid with low molecular weight can be purified, according to the invention by a method comprising the steps of (a) providing the nucleic acid in a lysed sample, whereby the sample is dissolved in a liquid composition comprising an aqueous buffer, TDE at a concentration between 5% and 30%, measured as volume by volume, a detergent and a chaotropic agent; followed by (b) providing a first solid phase, contacting the liquid composition of step (a) with the first solid phase, and separating the liquid phase from the first solid phase; followed by (c) mixing an additional amount of TDE with the liquid phase of step (b), thereby adjusting the concentration of TDE in the liquid phase of step (b) to between 20% and 70%, measured as volume by volume, whereby the initial concentration of TDE in the liquid phase is increased by a factor of 1.3 or more; followed by (d) providing a second solid phase and contacting the liquid composition of step (a) with the second solid phase; followed by (e) washing with a washing solution the second solid phase of step (d), whereby the washing solution comprises an organic solvent at a concentration of between 50% and 100%; followed by (f) contacting the second solid phase of step (e) with an aqueous desorption solution containing solutes in a lower concentration compared to the composition of step (a), thereby desorbing the nucleic acid from the solid phase and dissolving the nucleic acid in the solution; followed by (g) separating the solution with the nucleic acid from the solid phase, thereby purifying the nucleic acid; and optionally (h) precipitating the nucleic acid from the solution of step (f) and isolating the precipitated nucleic acid, thereby further purifying or concentrating the nucleic acid.

In step (a), a concentration of TDE at about 20% [v/v] is most preferred. Basically, in this method nucleic acids which are not desired due to their larger size are adsorbed, onto the first solid phase and removed from the liquid phase. However, the conditions applied still retain nucleic acids of the desired size in solution. Nucleic acids of the desired size are adsorbed to the second solid phase upon mixing further additive to the solution. Preferably, further TDE is added. The final TDE concentration in the adsorption solution for the second solid phase is preferably in the range of between 30% [v/v] and less than 100% [v/v]. A more preferred range for the final concentration of TDE in this step is between 30% [v/v] and 80% [v/v], even more preferred between 30% [v/v] and 60% [v/v], between 30% [v/v] and 50% [v/v]; most preferred the final TDE concentration in step (c) is about 40%, measured as volume by volume.

According to the invention, in step (c) the initial TDE concentration [i.e. the TDE concentration in the liquid composition of step (a)] is increased by a factor of 1.3 or more to result in a final TDE concentration of one the above specified preferred concentration ranges. For example, if the initial concentration of TDE is 20%, the final TDE concentration in the liquid composition of step (c) has to be 20% [v/v] *1.3=26% [v/v] at minimum. If, by way of another example, the initial TDE concentration is 5%, the final TDE concentration in the liquid composition of step (c) is calculated with a factor higher than 1.3, in order to reach the minimally required TDE concentration of 20%. Accordingly, the factor does not exceed 14 since the highest final TDE concentration in the composition of step (c) is 70%. Thus, the value of the factor is between 1.3 and 14.

The washing solution may additionally comprise an aqueous buffer which buffers the pH of the washing solution at a value between 4.0 and 7.5.

In view of the invention, a nucleic acid of low molecular weight is preferably characterized in that (a) the nucleic acid is single-stranded and the size of the purified nucleic acid is between 10 bases and 150 bases; or (b) the nucleic acid is double-stranded and the size of the purified nucleic acid is between 5 bases and 75 bases. Very much preferred, the nucleic acid of low molecular weight is DNA or RNA. Even more preferred, the nucleic acid of low molecular weight is single-stranded or double-stranded RNA.

The detergent which can be used in the adsorption solution aids in the process of releasing the nucleic acids. E.g., cells and tissues are lysed by detergents which disintegrate cellular membranes. In addition, detergents enhance the dissociation of nucleic acids from concomitant sample constituents such as protein. In addition, a detergent increases the binding of nucleic acids to solid phases, and when using a porous solid phase the detergent facilitates access of the liquid phase to the pore compartments of the solid phase.

The solid phases which can be preferably used for the purification of low molecular weight nucleic acids are generally the same as for the general nucleic acid purification procedure according to the invention. A solid phase with a silica surface is most preferred, however. A very much preferred pH range of an adsorption solution for a low molecular weight nucleic acid is between 4.0 and 7.5.

In order to reverse the conditions for adsorption, the concentration of the chaotropic agent and/or TDE is decreased resulting in desorption of the nucleic acid(s) bound to the solid material. Thus, the invention also encompasses the method comprising the step of releasing the adsorbed nucleic acid (=desorbing) from the solid phase. Preferably, the process of separating the substrate, e.g. the magnetic glass particles, from the rest of the sample is done by pelleting the immobilized biological material, e.g. by gravity force or by the use of a magnet in the case of magnetic glass particles, and removal of the supernatant. Then the magnetic glass particles with the immobilized biological material are resuspended in an aqueous solution with no or only a low amount of chaotropic agent and/or TDE. Alternatively, the suspension can be diluted with a solution with no or only a low amount of chaotropic agent and/or TDE. Buffers of this nature are known from DE 37 24 442 and Jakobi, R., et al, Anal. Biochem. 175 (1988) 196-201. An elution buffer, i.e. a desorption solution, has a low salt content and preferably a pH greater than 7.5, a pH of about 8 being most preferred. Preferably the desorption solution contains solutes in a lower concentration compared to the adsorption solution. Particularly preferred, the solutes are one or more buffer salts with a content of less than 0.2 M of dissolved matter. Thus, the preferred concentration of solutes in the desorption solution is in between 0 M and 0.2 M. In addition, the preferred desorption solution does not contain a chaotropic agent or an organic solvent such as TDE. Preferably, the elution buffer contains the substance TRIS for buffering purposes. Also very much preferred, the elution buffer is demineralized water. The solution containing the purified nucleic-acid(s) can now be used for other reactions. Optionally, the nucleic acid(s) can be precipitated from the solution using, e.g., ethanol or isopropanol. The precipitate can also be subjected to further washing steps. Methods of this kind are well known to the skilled artisan are described in detail in Sambrook, Fritsch & Maniatis, Molecular Cloning, A Laboratory Manual, 3rd edition, CSHL Press, 2001.

For the desorption step conditions are chosen by the skilled artisan, under which the nucleic acids are released from the mineral support. Preferably, greater than 40%, more preferred greater than 50%, more preferred greater than 70%, more preferred greater than 80%, even more preferred greater than 90%, even more preferred greater than 95%, even more preferred greater than 99% of the nucleic acids are released from the mineral support.

Purification of a nucleic acid by way of adsorbing the same to a substrate such as a mineral substrate in the presence of a composition according to the invention can also applied to other complex mixtures. Examples therefor are known to the person skilled in the art of molecular biology and include reaction mixtures following, e.g., in-vitro synthesis of nucleic acids such as PCR, restriction enzyme digestions, ligation reactions, etc. Another application for purification of a nucleic acid by way of adsorbing the same to a solid phase in the presence of a composition according to the invention is the removal of pyrogenic contaminants which may have copurified with the nucleic acid.

With great advantage, the method according to the present invention is suitable for the purification of nucleic acids, i.e. RNA or DNA, from complex mixtures with other biological substances containing them. Thereby also mixtures of different nucleic acids may be purified, even mixtures containing a nucleic acid of interest in low abundance. Thus, the present invention also encompasses the purification of mixtures of specific nucleic acids in which the target nucleic acid(s) may be a minor component in terms of concentration (or may be present in low abundance).

The procedure described can also be used to isolate native or modified nucleic acids. Native nucleic acids are understood to be nucleic acids, the structure of which was not irreversibly changed compared with the naturally-occurring nucleic acids. This does not mean that other components of the sample can not be modified, however. Modified nucleic acids include nucleic acids that do not occur in nature, e.g., nucleic acids that are modified by attaching to them groups that are reactive, detectable or capable of immobilization. An example of this are biotinylated nucleic acids.

The invention also contemplates kits. Such kits known to the art comprise plasticware useful in the sample preparation procedure. Examples therefor are microwell plates in the 96 or 384 well format or just ordinary reaction tubes manufactured e.g. by Eppendorf, Hamburg, Germany. The kits of the invention also comprise some or all other reagents for carrying out the methods according to the invention. Therefore, a kit can additionally contain a solid phase, i.e. a material with an affinity to nucleic acids. Preferably the solid phase comprises a material with a silica surface. Very much preferred, the solid phase comprises glass or quartz fibers. Also very much preferred, the solid phase is a composition comprising magnetic glass particles, i.e. magnetically attractable particles coated with glass. Another preferred material with an affinity to nucleic acids is anion exchanger. The kit can further or additionally comprise a lysis buffer containing e.g. a chaotropic agent, a detergent or mixtures thereof. These components of the kit according to the invention may be provided separately in tubes or storage containers. Depending on the nature of the components, these may be even provided in a single tube or storage container. The kit may further or additionally comprise a washing solution which is suitable for the washing step of the solid phase when DNA or RNA is bound thereto. This washing solution may contain TDE according to the invention and/or a chaotropic agent in a buffered solution or solutions with an acidic pH without TDE and/or a chaotropic agent as described above. Often the washing solution or other solutions are provided as stock solutions which have to be diluted before use. The kit may further or additionally comprise a desorption solution, i.e. an elution buffer, that is to say a solution for desorbing the nucleic acid from the solid phase. A preferred desorption solution can be a buffer (e.g. 10 mM Tris, 1 mM EDTA, pH 8.0) or pure water. Further, additional reagents or buffered solutions may be present which can be used for the purification process of a nucleic acid, i.e. DNA or RNA.

A further aspect of the invention is a kit of parts, comprising packaging material, containers, and (a) TDE, (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, an alkali halogenide, and mixtures thereof; and (c) chromatographic and filtering material comprising a material with a surface capable of interacting with the phosphate residues in the backbone of nucleic acids.

A preferred embodiment of the present invention is to: use the methods or the kits of the present invention in automatable methods as e.g. described in WO 99/16781. Automatable method means that the steps of the method are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to be filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. Preferred automated methods are those which are carried out in a high-throughput format which means that the methods and the used machine or apparatus are optimized for a high-throughput of samples in a short time. In another embodiment of the invention the methods or the kits according to the present invention are used in a semi-automated process which means that some reaction steps may have to be done manually. In a preferred embodiment of the invention, a suspension containing magnetic glass particles according to the present invention is taken from a storage container and partial volumes are added to different reaction vessels. Reaction vessels may be reaction tubes made from plastics eventually in microwell plate format contain 96 or 384 or more wells where a reaction can be carried out. However, these vessels may be made from other material, e.g. from steel.

A further aspect of the invention is a kit of parts, comprising packaging material, containers, and (a) a suspension of silica-coated magnetic particles in TDE; and (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, and an alkali halogenide.

Some of the organic compounds contemplated by the invention might be capable of dissolving certain plastic materials. Thus, when determining the nature of suitable storage or reaction vessels, the skilled artisan will determine in a limited number of obvious experiments the material which is suited best for executing the methods of the invention or for producing kits according to the invention.

In preferred embodiments of the invention the kits according to the invention are used for the purification of nucleic acids in research, bioanalytics or diagnostics. In preferred embodiments according to the invention the kits according to the invention or the methods according to the invention are used in a high-throughput format, i.e. in an automated method which allows the analysis of a high number of different samples in a very short time.

The nucleic acids isolated using the methods according to the invention can be used further as necessary. For instance, they can be used as a substrate for various enzymatic reactions. The nucleic acids can be used for a large number of purposes including sequencing, radioactive or non-radioactive labelling, amplification of one or more of the sequences they contain, transcription, hybridization with labelled probe nucleic acids, translation or ligation.

Yet, a further aspect of the invention is a method for determining the presence of a nucleic acid in a sample, comprising the steps of: (a) optionally lysing the sample; (b) forming a composition containing (i) the sample or the lysed sample of step (a), (ii) an aqueous buffer, (iii) a chaotropic agent, and (iv) TDE, whereby the sample is dissolved in the liquid composition; (c) contacting the composition of step (b) with a solid phase, thereby adsorbing the nucleic acid onto the solid phase; (d) separating the solid phase with the adsorbed nucleic acid from the liquid phase; (e) optionally washing with a washing solution the solid phase with the adsorbed nucleic acid; followed by (0 contacting the solid phase with the adsorbed nucleic acid with an aqueous desorption solution containing solutes in a lower concentration compared to the composition of step (b), thereby desorbing the nucleic acid from the solid phase and dissolving the nucleic acid in the solution; followed by (g) separating the solution with the nucleic acid from the solid phase, thereby purifying the nucleic acid; and (h) detecting in the solution of step (g) the presence of the nucleic acid, thereby determining the presence of the nucleic acid.

It is preferred that the sample is a biological sample. Preferably, the nucleic acid is determined by amplification of the nucleic acid by means of the polymerase chain reaction using specific primers, a specific detection probe, and an amplification mixture, whereby amplification is monitored in real time. Also preferred is to determine the nucleic acid by hybridizing the nucleic acid to a hybridization probe and detecting and/or quantifying the hybrid. The skilled artisan is aware of the fact that not only a nucleic acid can serve as a hybridization probe but also a nucleic acid comprising one or more nucleoside analogues can be used. In addition, nucleic acid analogues such as PNA are known to the art as being capable of forming detectable hybrids with nucleic acids. It is understood that nucleic acid to be determined is DNA or RNA. Very much preferred is the above method, whereby the nucleic acid is. RNA and step (h) comprises (i) reverse transcribing the RNA to form a cDNA, (ii) subsequently amplifying, by means of the polymerase chain reaction, the cDNA, (iii) detecting the presence of the cDNA, thereby determining the presence of the nucleic acid.

The following examples and figures are provided to aid the understanding of the present invention, the true scope of which is set forth in the appended claims. It is understood that modifications can be made in the procedures set forth without departing from the spirit of the invention.

All Examples given below were performed as variations of the standard workflow of the HIGH PURE (Roche Diagnostics Operations, Inc.) PCR Template Preparation Kit, user manual version April 2005, Roche Diagnostics GmbH, Mannheim, Germany, Catalogue No. 11796828001. Unless indicated otherwise, all working steps of the workflow were performed as indicated in said user manual.

Example 1

Purification of Total Nucleic Acids from Blood Samples

The workflow for purification of the nucleic acids (NAs) includes the following steps: Lysis of the sample in order to make the nucleic acids accessible for the purification process. Adsorption of the NAs onto the solid phase, separating the solid phase from the liquid phase and washing the solid phase with the bound NAs, and desorbing the NAs from the solid phase.

Each sample consisted of a volume of 200 µl of EDTA whole blood. The solid phase used was silica fleece present in HIGH PURE spin columns (Roche Diagnostics GmbH, Mannheim, Germany). Compounds tested for binding enhancement to the silica fleece were selected from Table 1, except those that show toxic properties. Toxic compounds were excluded.

EDTA blood was pooled and aliquots were subjected to nucleic acid isolation according to the following protocol: 200 µl whole EDTA blood was mixed with 200 µl Binding Buffer (6 M guanidine HCl, 100 mM MES, 18.5% [v/v] TRITON X-100, pH 5.7) and 40 µl Proteinase K (20 µg/µl dissolved in bidestilled water) solution. The mixture was incubated for 10 min at 70° C. to effect lysis. Afterwards, 100 µl of one of the substances listed in Table 2 was added to a lysed sample and mixed. The mixture was applied to a spin column (HIGH PURE spin column, Roche Diagnostics GmbH, Mannheim, Germany) for further processing. Handling of the columns as well as washing and elution was performed according to the package insert of the HIGH PURE PCR Template Preparation Kit, version April 2005 (Catalogue No. 11796828001 Roche Diagnostics GmbH, Mannheim, Germany).

TABLE 2

Yield and purity of nucleic acids obtained from 200 µl EDTA whole blood

| Substance | yield (ng) | purity | hazard classification |
|---|---|---|---|
| tetraethylene glycol dimethyl ether (TDE) | 3975.32 | 1.88 | |
| glycerolformal | 3856.59 | 1.84 | |
| diethylene glycol diethyl ether | 3697.14 | 1.87 | Xi |
| methyl ethyl ketone | 3606.98 | 1.87 | F, Xi |
| propylene glycol dimethylether (dimethoxypropane) | 3590.64 | 1.87 | F |
| ethylene glycol diethyl ether (diethoxyethane) | 3530.66 | 1.88 | Xi |
| propylene glycol monomethyl ether acetat | 3526.20 | 1.85 | Xi |
| tetrahydrofuran | 3399.51 | 1.88 | F, Xi |
| polyethylene glycol 1000 | 3307.32 | 1.93 | |
| 1,3 dioxolane | 2988.81 | 1.88 | F, Xi |
| hydroxyacetone | 2601.50 | 1.87 | |
| ethanol | 2572.52 | 1.90 | F |
| isopropanol | 2561.75 | 1.90 | F, Xi |
| ethyllactate | 2403.28 | 1.83 | Xi |
| acetone | 1884.73 | 1.89 | F, Xi |

Yield was determined by measuring OD at 260 nm and multiplying the extinction value with the factor of 50 (for double-stranded nucleic acids) or 40 (for single-stranded nucleic acids).

Purity was assessed by measuring the extinction of the eluate at 260 nm and 280 nm and calculating the 260/280 nm quotient.

Figure 1:
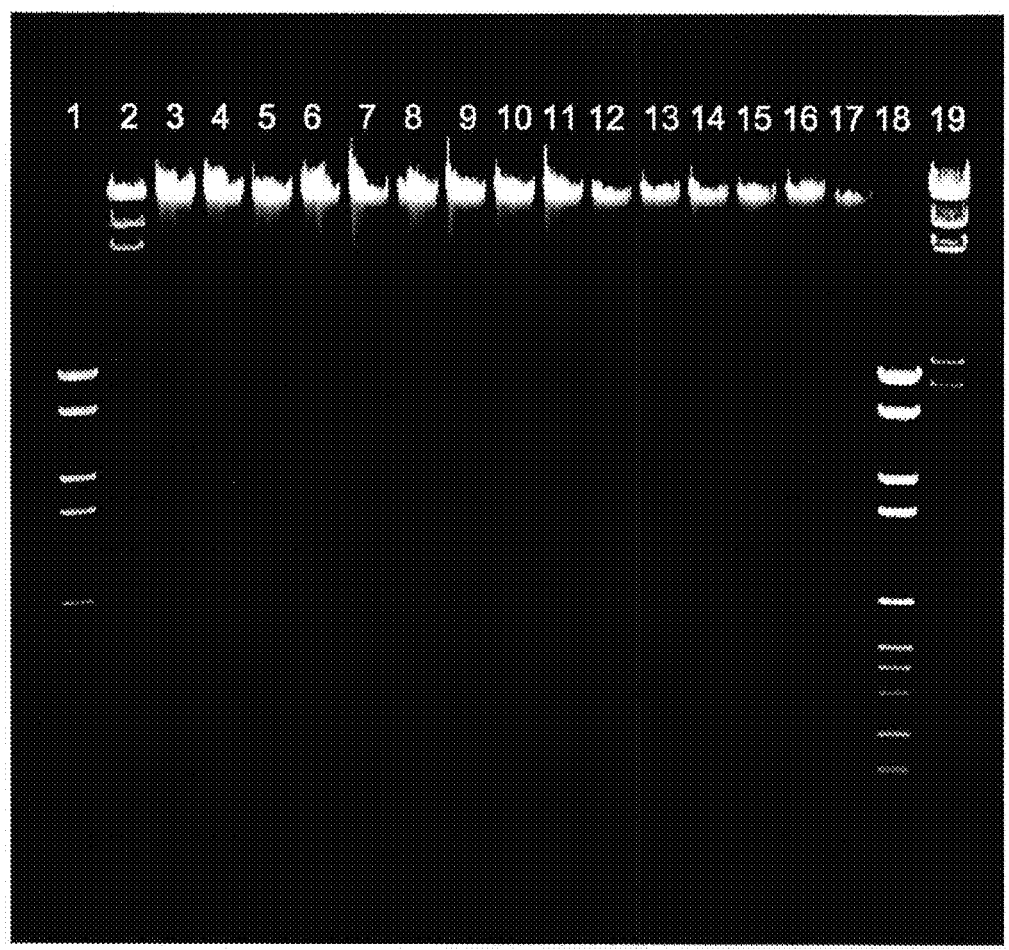
FIG. 1 Total nucleic acids isolated from EDTA whole blood with different binding additives (see Example 1) after 1% agarose gel electrophoresis and ethidium bromide staining. Similar volumes of eluate were applied. Each individual lane is numbered.

Integrity of the nucleic acids isolated by this method is shown in FIG. 1. In conclusion, use of Tetraethylene Glycol Dimethyl Ether (TDE) as well as glycerolformal lead to superior yield of nucleic acids isolated from 200 µl of whole EDTA blood compared to other substances. At the same time, these two compounds are particularly advantageous due to their very low or even lacking toxicity.

Example 2

Purification of Total Nucleic Acids from Tissue Culture Cells

The workflow for purification of the nucleic acids (NAs) includes the following steps: Lysis of the sample in order to make the nucleic acids accessible for the purification process. Adsorption of the NAs onto the solid phase, separating the solid phase from the liquid phase and washing the solid phase with the bound NAs, and desorbing the NAs from the solid phase.

Total nucleic acids were purified from $1 \times 10^6$ K562 cells. Sedimented cells were resuspended in 200 µl PBS buffer. Afterwards 200 µl binding buffer (6 M guanidine HCl, 100 mM MES, 18.5% [v/v] TRITON X-100, pH 5.7) and a measured amount of TDE (final concentration of TDE: 10%, 20% and 40% [v/v]) were added and mixed. Each sample was applied to a spin column (HIGH PURE spin column, [CATA-LOG #] Roche Diagnostics GmbH, Mannheim, Germany)

and processed according to standard procedure (HIGH PURE PCR Template Preparation Kit, user manual version April 2005, Roche Diagnostics GmbH, Mannheim, Germany, Catalogue No. 11796828001). For combinatorial use of TDE and glycerol formal a similar experimental workflow was used. Only the binding buffer was changed to 6 M guanidine HCl, 100 mM MES, 10% [v/v] glycerol formal, 18.5% [v/v] TRITON X-100, pH 5.7. Results of this experiment are shown in FIG. 2. By using a combination of TDE and glycerolformal in the purification process the nucleic acid yield could be increased compared with the use of TDE only.

Example 3

Purification of Nucleic Acids from Tissue Culture Cells

Nucleic acids were purified from 1×10$^6$ K562 cells. Sedimented cells were resuspended in 200 µl PBS buffer. Afterwards 200 µl binding buffer (6 M guanidine HCl, 100 mM MES, 18.5% [v/v] TRITON X-100, pH 5.7) and 100 µl TDE were added and mixed. Each sample was applied to a spin column (HIGH PURE spin column, Roche Diagnostics GmbH, Mannheim, Germany) and processed according to standard procedure (HIGH PURE PCR Template Preparation Kit, user manual version April 2005, Roche Diagnostics GmbH, Mannheim, Germany, Catalogue No. 11796828001). A first and a second washing buffer were used consecutively in each isolation/purification process. To prepare the first washing buffer (inhibitor removal buffer) a volume of 20 ml TDE or ethanol is added to a volume of 33 ml concentrated stock solution of washing buffer 1 to form a buffer in which the final concentration of TDE or ethanol is about 39% [v/v], along with the remaining ingredients 5 M guanidine HCl, 20 mM Tris HCl, pH 6.6 (25° C.) (final concentrations after the addition of TDE/ethanol). To prepare the second washing buffer (desalting buffer) ethanol or TDE were added to a stock solution of washing buffer 2 to form a buffer in which the final concentration of TDE or ethanol is about 80% [v/v], along with the remaining ingredients 20 mM NaCl, 2 mM Tris HCl, pH 7.5 (25° C.) (final concentrations after the addition of TDE/ethanol). Comparisons were made, whereby three washing steps were applied to each sample, either with ethanol-containing or with TDE-containing wash buffers. The first washing step was performed with the first washing buffer, followed by two washing steps with the second washing buffer. Subsequently, the nucleic acids were desorbed from the solid phase. Except for the details given above, all steps further steps of the workflow were performed according to the standard procedure provided by the manufacturer (see manual for the HIGH PURE PCR Template Preparation Kit, user manual version April 2005, Roche Diagnostics GmbH, Mannheim, Germany).

TABLE 3

Comparison of TDE and ethanol as additives in the washing buffers

| sample | yield [µg] |
|---|---|
| Nucleic acid from K562 cells using ethanol in washing buffers | 22.43 |
| Nucleic acid from K562 cells using TDE in washing buffers | 22.62 |

Yield was determined as described in Example 1.

FIG. 3 depicts an agarose gel which was run with the isolated nucleic acids in order to demonstrate their integrity.

Example 4

Recovery of dsDNA of a Size Between 50 bp and 400 bp from an Aqueous Phase

In order to specifically monitor the recovery of dsDNA fragments of a size between 50 bp and 400 bp a solution containing 1.5 µg of a 50 bp and 1.5 µg of a 400 bp fragment was used in the experiment. 100 µl of the DNA solution was mixed with 200 µl binding buffer (3 M guanidine SCN, 6.25% [v/v] Dioxolan 200 mM BES, 7.5% [v/v] TRITON, pH 7.0) and 200 µl TDE. After binding the washing procedure was performed as described in Example 3, Again, ethanol was compared to TDE in the washing buffers. Table 4 indicates the results.

TABLE 4

Isolation of small DNA molecules, comparison of TDE and ethanol as additives in the washing buffers

| sample | yield [µg] | recovery [%] |
|---|---|---|
| Purified DNA fragments using ethanol in washing buffers | 2.98 | 87.86 |
| Purified DNA fragments using TDE in washing buffers | 3.13 | 92.27 |

Yield was determined as described in Example 1.
The integrity of the nucleic acids isolated/purified with the above procedure is shown in FIG. 3.

Example 5

Evaporation of Additives from Liquid Compositions

The effect of evaporation of organic solvents as additives in liquid compositions for the isolation/purification of nucleic acids was investigated. Several compositions were tested, whereby the compositions included organic solvents with differences in vapor pressure indicating a different evaporation rate. Evaporation affects stability of a reagent as well as reproducibility of the process in which the reagent is used. This is especially true in the case of automated systems for nucleic acid purification.

The evaporation rate of buffers with different compositions was determined. A volume of 200 µl of water was mixed with 200 µl binding buffer containing 6 M guanidine-HCl, 10 mM urea, 10 mM Tris HCl, 20% TRITON X-100 (v/v), pH4.4 (25° C.) and 100 µl of a substance listed below in Table 5. Incubation of the mixtures was carried out for 30 mM at 30° C. in a standard 1.5 ml eppendorf tube, whereby the lid was left open. Evaporation was assessed by weighing each tube before and after incubation and tabulating weight loss.

TABLE 5

Evaporation of different substances after 30 min from 20% [v/v] solutions

| Substance | vapor pressure at 20° C. [in mm Hg] | weight loss [in µg] |
|---|---|---|
| Tetraethylene Glycol Dimethyl Ether (TDE) | <0.01 | 3.3 |
| Diethylene Glycol Diethyl Ether | 0.5 | 3.3 |
| Ethyllactat | 2 | 3.6 |
| Hydroxyaceton | 5.6 | 4.7 |
| Glycerolformal | n/a | 5.2 |
| Diethylene Glycole Dimethyl Ether | 3 | 6.0 |

TABLE 5-continued

Evaporation of different substances after 30 min from 20% [v/v] solutions

| Substance | vapor pressure at 20° C. [in mm Hg] | weight loss [in µg] |
| --- | --- | --- |
| Polyethylene Glycol 1000 | n/a | 8.2 |
| Propylene Glycol Monomethyl Ether Acetate | 3.7 | 8.3 |
| Ethanol | 44.6 | 9.3 |
| Isopropanol | 33 | 14.0 |
| Ethylene Glycol Diethyl Ether | 9.4 | 14.4 |
| 1,3 Dioxolane | 70 | 21.1 |
| Propylene Glycol Dimethyl Ether | 40 | 21.5 |
| Metyl Ethyl Ketone | 71 | 28.6 |
| Acetone | 184 | 32.3 |
| Tetrahydrofuran | 143 | 44.4 |

When analyzing the amounts of weight loss one has to appreciate that the evaporated matter may also comprise water, apart from the organic solvent tested. The highest loss was observed for the Tetrahydrofuran containing buffer. Approximately 44.4 µg were evaporated from the 500 µl volume after 30 minutes. However, from the TDE containing buffer only approximately 3.3 µg evaporated. This example demonstrates the superior properties of substances with low vapor pressure, particularly that of TDE, compared with substances displaying a high evaporation rate (i.e. Tetrahydrofuran, Acetone, etc.).

Example 6

Automated Nucleic Acid Isolation/Purification Workflow

For the demonstration of an automated workflow a MagnaPure LC instrument (Roche Diagnostics GmbH, Mannheim, Germany) was used for the evaluation. Total nucleic acids were purified from $10^6$ cultured K562 cells. For the procedure the MAGNA PURE LC (Roche Diagnostics Operations, Inc.) DNA Isolation Kit—Large Volume (Roche Diagnostics GmbH, Mannheim, Germany) was used. The standard procedure according to the instructions by the supplier using magnetically attractable particles dissolved in isopropanol was compared to a procedure with a similar amount of magnetic particles, however dissolved in TDE or Diethylene Glycol Diethyl Ether. Apart from this variation, the workflow was performed exactly according to the package insert of the MAGNA PURE LC DNA Isolation Kit—Large Volume (Version May 2006), Cat No 03310515001.

TABLE 6

Yield and purity of nucleic acid isolated from $10^6$ K562 cells using the MAGNA PURE instrument and various additives in the adsorption solution

| Magnetic particles dissolved in | Yield (µg) |
| --- | --- |
| Tetraethylene Glycol Dimethyl Ether | 18.4 |
| Isopropanol | 10.8 |
| Diethylene Glycol Diethyl Ether | 8.1 |

Yield was determined as described in Example 1.

Table 5 displays average values obtained in 4 experimental runs each. In the automated workflow of the MAGNA PURE instrument tetraethylene glycol dimethyl ether showed a better performance compared with isopropanol and diethylene glycol diethyl ether. Integrity of the isolated nucleic acids was tested by size separation using agarose gel electrophoresis and ethidium bromide staining (see FIG. 4).

Example 7

Binding of Nucleic Acid Molecules of Various Sizes Using Different TDE Concentrations in the Binding Step Nucleic acids of various sizes from a biological sample were mixed with small RNA molecules (in this case with microRNA, =miRNA). The experimental setting was designed to determine under which conditions small nucleic acids below 150 bases can be isolated together with nucleic acids of larger sizes. Samples consisting of either (i) $10^6$ K562 cells or (ii) 1 µg of pre-purified miRNA 16 (supplied by Metabion, Martinsried, Germany) were dissolved separately in 300 µl binding buffer "C45G45T" containing 200 mM sodium citrate pH 4.5, 4.5 M guanidine SCN, and 2.5% [v/v] TRITON X-100. Then the two samples were mixed in equal volumes. TDE was added to the solution to a final concentration of between 35% [v/v] and 55% [v/v], and mixed for 10 s on a Vortex mixer. Each mixture was subsequently applied to a HIGH PURE column from the HIGH PURE PCR Product Purification Kit (Roche Diagnostics GmbH, Mannheim, Germany, 41 732 668 001). The columns were centrifuged for 30 s at 13,100×g. The flow-throughs were discarded. The columns were then washed with 500 µl of the ethanol reconstituted washing buffer supplied with the HIGH PURE PCR Product Purification Kit. After adding ethanol, the reconstituted washing buffer consisted of 80% [v/v] ethanol, 20 mM NaCl, 2 mM Tris-HCl pH 7.5. Elution was subsequently performed with 100 µl desorption buffer containing 10 mM Tris-HCl pH 8.5. A 10 µl aliquot of each fractions was electrophoresed on 15% acrylamide gels with TBE/Urea runnig buffer (Invitrogen).

FIG. 5 shows that a concentration of 40% TDE was necessary for optimum binding of the miRNA, whereas higher molecular weight nucleic acids were bound also at a lower TDE concentration.

Example 8

Purification of Low Molecular Weight Nucleic Acid Molecules Using Two Consecutive Separations with Spin Columns Small nucleic acids with sizes lower than 150 nucleotides (i.e. microRNA) were separated from a biological sample containing nucleic acid molecules of various sizes. Samples consisting of either $10^6$ K562 cells or 1 µg of chemically synthesized miRNA 16 were dissolved separately in 300 µl binding buffer "C45G45T" containing 200 mM sodium citrate pH 4.5, 4.5 M guanidine SCN, and 2.5% [v/v] TRITON X-100. Then the two samples were mixed in equal volumes. TDE was added to the solution to result in a final concentration of between 0% [v/v] and 30% [v/v], and mixed for 10 sec. Each mixture was subsequently applied to a HIGH PURE column from the HIGH PURE PCR Product Purification Kit (Roche Diagnostics GmbH, Mannheim, Germany, 11 732 668 001). The columns were centrifuged for 30 s at 13,100×g. The flow-throughs were collected and TDE was added to a final concentration of 40% TDE in each sample. After mixing for by vortexing for 10 s the mixtures were applied onto a second set of HIGH PURE columns and centrifuged for 30 s at 13,100×g. The first and second set of columns were then washed two times with each 500 µl of washing buffer consisting of 80% [v/v]ethanol, 20 mM NaCl, 2 mM Tris-HCl pH 7.5 from the HIGH PURE PCR Product Purification Kit. Elution was subsequently performed with 100 µl desorption buffer containing 10 mM Tris-HCl pH 8.5.

10 µl aliquots of all fractions (eluates from the first and second columns) were electrophoresed in 15% acrylamide gels with TBE/Urea runnig buffer (Invitrogen).

FIG. 6 A shows that on the first column miRNA is not bound efficiently at concentrations of less than 30% TDE concentration, in contrast to nucleic acids with higher molecular weight. miRNA is therefore not apparent in eluates from the first column. It is bound however at a concentration of 40% TDE onto the second column. FIG. 6 B shows that miRNA elutes from the second column. Particularly, it can be seen that in lane 10 (30% TDE on first column) only miRNA is eluted from the second column. The miRNA is essentially purified from larger nucleic acid species.

Example 9

Nucleic Acid Isolation and Subsequent Detection

Small nucleic acid molecules of sizes smaller than 150 nucleotides (i.e. microRNA) were isolated from liver and kidney tissue and detected using a Q-RT-PCR (quantitative-reverse transcription-polymerase chain reaction) protocol.

Samples of small pieces of mouse liver or kidney tissue were frozen in liquid nitrogen and pulverized in a cooled mortar. Aliquots of 10 mg samples were then dissolved in 300 µl of Binding buffer "M55G45T" containing 500 mM MES pH 5.5, 4.5 M guanidine SCN, 2.5% [v/v] TRITON X-100.

Then either a single column procedure was applied to isolate total nucleic acids or a procedure with two consecutive columns was followed, in order to purify miRNA from total nucleic acids.

Single Column Protocol:

To a volume of 300 µl of each lysed sample (prepared as descried above) TDE was added to result in a final concentration of 40% [v/v], and mixed for 10 sec. The whole mixtures were then applied onto HIGH PURE columns from the HIGH PURE PCR Product Purification Kit (Roche), 11 732 668 001 and spun for 30 s at 13,100×g. The flow-throughs were discarded. The columns were washed two times with each 500 µl washing buffer consisting of 80% [v/v]ethanol, 20 mM NaCl, 2 mM Tris-HCl pH 7.5 from the HIGH PURE PCR Product Purification Kit. Elution, was subsequently performed with a volume of 100 desorption buffer per column, containing 10 mM Tris-HCl pH 8.5.

Procedure with Two Consecutive Columns:

To a volume of 300 µl of each lysed sample (prepared as descried above) TDE was added to result in a final concentration of 20% [v/v], and mixed for 10 sec. The whole mixtures were then applied onto HIGH PURE columns from the HIGH PURE PCR Product Purification Kit (Roche), 11 732 668 001 and spun for 30 s at 13,100×g. The flow-throughs were collected. TDE was added to each flow-through sample, to result in a final TDE concentration of 40% [v/v] in each sample. After mixing by vortexing for 10 s each mixture was applied onto a second HIGH PURE column. Each column was then centrifuged for 30 s at 13,100×g. Each column of the first and second set was washed two times with a volume of 500 µl of washing buffer consisting of 80% [v/v]ethanol, 20 mM NaCl, 2 mM Tris-HCl pH 7.5 from the HIGH PURE PCR Product Purification Kit. Elution was subsequently performed with a volume of 100 µl desorption buffer per column, containing 10 mM Tris-HCl pH 8.5.

10 ng of total RNA nucleic acids as purified with the one column protocol and the same aliquot of the original sample from the purified small nucleic acids fraction (containing miRNA) from the two column protocol (see Example 8) were reverse transcribed and PCR amplified on the LightCycler 480 from Roche using the hsa-let-7a miRNA Kit with the TaqMan MicroRNA Assay Protocol of Applied Biosystems. The primer for the reverse transcription and the PCR primers were contained in the Applied Biosystems Kit.

In FIG. 7 the result of the PCR amplification on the LightCycler 480 is shown. It can be seen that the 1 column protocol as well as the 2 column protocol yield signals at similar amplification cycles (CP values) for the liver tissue CP 21.89 (with the single column protocol, see Example 7) as compared to CP 21.55 (with two column protocol). With kidney tissue the cp for the purified miRNA sample was earlier CP 20.89 (with two column protocol) as compared to the sample with the total nucleic acid CP 21.72 (with one column protocol). The negative controls without Reverse Transcriptase and no template control yielded no signals for all isolated RNA samples, as expected. This demonstrates, that the purification protocol is compatible with the subsequent reverse Transcription and the detection in the PCR amplification steps.

Example 10

Isolation of Small Nucleic Acids from Tissue, Including Proteinase K Digestion

Samples of small pieces of mouse liver tissue were frozen in liquid nitrogen and pulverized in a cooled mortar. Aliquots of 10 mg samples were then dissolved in 100 µl Tissue Lysis Buffer [consisting of 4 M Urea, 100 mM NaCl, 260 mM EDTA, 200 mM Tris-HCl, pH 7.3-7.4] from the HIGH PURE RNA Paraffin Kit (Roche), catalog no. 03 270 289 001. Then 16 µl 10% SDS and 40 µl Proteinase K working solution from the HIGH PURE RNA Paraffin Kit (Roche), catalog no. 03 270 289 001) were added to each sample.

The samples were then vortexed three times, each time for 5 s, and incubated for 1 h at 55° C. Then 325 µl of Binding Buffer [consisting of 5 M GuSCN, 50 mM Tris-HCl, 20% TRITON X-100 (w/v), 1% DTT (w/v), pH 6.0] from the HIGH PURE RNA Paraffin Kit (Roche), catalog no. 03 270 289 001 and 325 µl TDE were added and vortexed for 3×5 s. The final pH of that mixture was 7.3.

The mixtures were then applied onto HIGH PURE columns from the HIGH PURE PCR Product Purification Kit (Roche), catalog no. 11 732 668 001 and spun for 30 s at 13,100×g. The flow-throughs were collected. TDE was added to each flow-through sample, to result in a final TDE concentration of 40% [v/v] in each sample. After mixing by vortexing for 10 s each mixture was applied onto a second HIGH PURE column. Each column was then centrifuged for 30 s at 13,100×g. Each column of the first and second set was washed two times with a volume of 500 µl of washing buffer [consisting of 80% [v/v]ethanol, 20 mM NaCl, 2 mM Tris-HCl pH 7.5] from the HIGH PURE PCR Product Purification Kit. Elution was subsequently performed with a volume of 100 µl desorption buffer per column, containing 10 mM Tris-HCl pH 8.5.

A 10 µl aliquot of each fraction was electrophoresed on 15% acrylamide gels with TBE/Urea runnig buffer (Invitrogen).

FIG. 8 shows that a concentration of 20% TDE was necessary on the first column to bind all larger nucleic acid species (lanes 6 and 10), while at lower TDE concentrations larger nucleic acids copurified with the miRNA (lanes 4 and 5). At 25% TDE concentration on the first column already some miRNA was bound to the first column (lane 11).

Example 11

Recovery of Small Nucleic Acid Molecules from Silica Following Adsorption at Different pH Values Samples were prepared with different pH values adjusted. Each sample consisted of an adsorption solution containing 2 µg dsDNA with a size of about 400 bp and 2 µg dsDNA with a size of about 50 bp (resulting in a total of 4 µg of nucleic acid molecules in each sample), 1.6 M guanidine isothiocyanate, 20 mM MES, and 40% [v/v] TDE. Samples were identically prepared with the exception that different pH values were adjusted. The adsorption solutions were applied to HIGH PURE columns from the HIGH PURE PCR Product Purification Kit (Roche), catalog no. 11 732 668 001 and spun for 30 s at 13,100×g. Each column was washed once with a volume of 500 µl of washing buffer [consisting of 80% [v/v] ethanol, 20 mM NaCl, 2 mM Tris-HCl pH 7.5] from the HIGH PURE PCR Product Purification Kit. Elution was subsequently performed with a volume of 100 µl desorption buffer per column, containing 10 mM Tris-HCl pH 8.5.

The yield of nucleic acids obtained at different pH values is given in Table 7. As shown, good yields were obtained at all pH values given.

TABLE 7

DNA yield in relation to pH in the adsorption solution

| pH value of adsorption solution | yield [µg] |
|---|---|
| pH 4.5 | 3.52 |
| pH 5.0 | 3.41 |
| pH 5.5 | 3.13 |
| pH 6.5 | 3.31 |
| pH 7.0 | 3.68 |

What is claimed is:

1. A method for purifying a nucleic acid with low molecular weight comprising the steps of:
    providing a sample comprising a nucleic acid with low molecular weight and a nucleic acid with undesired molecular weight,
    dissolving the sample in a liquid composition comprising an aqueous buffer, tetraethylene glycol dimethyl ether (TDE) at a concentration between 5% and 30% by volume, a detergent, and a chaotropic agent,
    contacting the liquid composition containing the dissolved sample with a first solid phase whereby the nucleic acid with undesired molecular weight is adsorbed onto the solid phase, and separating the liquid composition from the first solid phase,
    adding additional TDE to the separated liquid composition from the previous step whereby the concentration of TDE is adjusted to between 20% and 70% by volume, thereby increasing the initial concentration of TDE in the liquid composition by a factor of 1.3 or more,
    contacting the adjusted liquid composition with a second solid phase whereby the nucleic acid with low molecular weight is adsorbed onto the second solid phase,
    washing the second solid phase with a washing solution comprising an organic solvent at a concentration of between 50% and 100%,
    contacting the second solid phase with an aqueous desorption solution containing solutes in a lower concentration than the liquid composition, thereby desorbing the nucleic acid with low molecular weight from the solid phase and dissolving the nucleic acid with low molecular weight in the desorption solution,
    separating the solution with the nucleic acid with low molecular weight from the solid phase, thereby purifying the nucleic acid with low molecular weight, and optionally precipitating the nucleic acid with low molecular weight from the solution and isolating the precipitated nucleic acid with low molecular weight, thereby further purifying the nucleic acid with low molecular weight, wherein the nucleic acid with low molecular weight is selected from the group consisting of single-stranded nucleic acids having a size between 10 and 150 bases and double-stranded nucleic acids having a size between 5 and 75 bases.

2. The method according to claim 1 wherein the nucleic acid with low molecular weight is RNA.

* * * * *

UNITED STATES PATENT AND TRADEMARK OFFICE
CERTIFICATE OF CORRECTION

| | | |
|---|---|---|
| PATENT NO. | : 8,124,338 B2 | Page 1 of 1 |
| APPLICATION NO. | : 12/481807 | |
| DATED | : February 28, 2012 | |
| INVENTOR(S) | : Donner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Fifteenth Day of May, 2012

David J. Kappos
*Director of the United States Patent and Trademark Office*